United States Patent
Banwell et al.

(10) Patent No.: US 6,521,757 B1
(45) Date of Patent: Feb. 18, 2003

(54) PREPARATION OF FUSED POLYCYCLIC ALKALOIDS BY RING CLOSURE OF AZOMETHINE YLIDES, NOVEL COMPOUNDS THEREOF AND THEIR USE AS CHEMOTHERAPEUTIC AGENTS

(75) Inventors: Martin Gerhardt Banwell, Aranda (AU); Bernard Luke Flynn, Griffith (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/423,167

(22) PCT Filed: May 1, 1998

(86) PCT No.: PCT/AU98/00312
§ 371 (c)(1),
(2), (4) Date: May 1, 2000

(87) PCT Pub. No.: WO98/50365
PCT Pub. Date: Nov. 12, 1998

(30) Foreign Application Priority Data

May 2, 1997 (AU) .............................................. PO 6565

(51) Int. Cl.$^7$ .................... C07D 491/147; C07D 217/00
(52) U.S. Cl. ........................... 546/47; 546/62; 546/139; 514/283; 514/285
(58) Field of Search ............................... 514/283, 285; 546/47, 62, 139

(56) References Cited

U.S. PATENT DOCUMENTS 5,852,033 A * 12/1998 Fernandez-Puentes et al. .. 514/283

FOREIGN PATENT DOCUMENTS

WO  WO 97/01336  1/1997  ......... A61K/31/435

OTHER PUBLICATIONS

Ueno et al. (1972) Bull. Chem. Soc. Japan 45(6):1797–1801.*
Haraoka et al. (1996) Chem. Abs. 64:14199c.*
Reddy, M.V.R. et al., "New Lamellarin Alkaloids from an Unidentified Ascidian from the Arabian Sea"; (1997) Tetrahedron 53:3457–3466..
Toyota, M. et al., "An Efficient Synthesis of 1,2,3,4–tetra–substituted Pyrroles via Intramolecular Azomethine Ylide [3+2] Dipolar Cycloaddition"; (1994) Heterocycles 39:No. 1, 39–42.
Urban, S. and Capon, R., "Lamellarin–S: a New Aromatic Metabolite from an Australian Tunicate, Didemnum sp."; (1996) Aust. J. Chem. 49:711–713.
Vedejs, E. and Piotrowski, D., "Oxazole Activation for Azomethine Ylide Trapping: Singly and Doubly Tethered Substrates"; (1993) J. Org. Chem. 58:1341–1348.
Andersen, R. et al., "Metabolites of the Marine Prosobranch Mollusc Lamellaria sp."; (1985) J. Am. Chem. Soc. 107:5492–5495.
Banwell, M. et al., "Convergent Total Synthesis of Lamellarin K"; (1997) Chem. Commun. 2259–2260.
Carroll, A. et al., "Studies of Australian Ascidians. I Six New Lamellarin–Class Alkaloids from a Colonial Ascidian, Didemnum sp."; (1993) Aust. J. Chem. 46:489–501.
Heim, A. et al., "Biomimetic Synthesis of Lamellarin G Trimethyl Ether"; (1997) Angew. Chem. Int. Ed. Engl. 36:No. 1/2 155–156.

(List continued on next page.)

Primary Examiner—Charanjit S. Aulakh
(74) Attorney, Agent, or Firm—Greenlee Winner and Sullivan, P.C.

(57) ABSTRACT

A method for the preparation of a compound of general Formula:

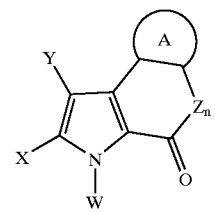

or pharmaceutically acceptable derivatives and salts, racemates, isomers and/or tautomers thereof comprising cyclizing an azomethine ylide of general Formula:

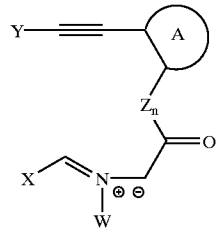

wherein,
A is a cyclic or non-cyclic group; Z is a carbon or a heteroatom; n is selected from 0, 1, 2, or 3; W, X and Y may be the same of different and each are selected from hydrogen; optionally substituted alkyl, alkenyl, alkynyl, amino, alkoxy, alkinoxy, alkynoxy, aryl, alkylthio, heterocyclyl; carboxy, carboxy ester, carboxamido, acyl, acyloxy, mercapto, halogen, nitro, sulfate, phosphate, cyano and optionally protected hydroxy; or W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group is provided.

48 Claims, No Drawings

OTHER PUBLICATIONS

Ishibashi, F. et al., "Total Synthesis of Lamellarin D and H. The First Synthesis of Lamellarin–Class Marine Alkaloids"; (1997) *Tetrahedron* 53:5951–5962.

Lindquist, N. and Fenical, W., "New Alkaloids of the Lamellarin Class from the Marine Ascidian *Didemnum chartaceum* (Sluiter, 1909)"; (1988) *J. Org. Chem.* 53:4570–4574.

Minguez, J.M. et al., "Pyrrolodiazines. 2. Structure and Chemistry of Pyrrolo[1,2–a] pyrazine and 1,3–Dipolar Cycloaddition of Its Azomethine Ylides"; (1996) *J. Org. Chem.* 61:4655–4665.

Minguez, J.M. et al., "Pyrrolodiazines. 4. Structure and Chemistry of 3,4–Dihydropyrrolo[1,2–a] pyrazine"; (1997) *Tetrahedron* 53:9341–9356.

Quesada, A.R. et al., "Polyaromatic Alkaloids from Marine Invertebrates as Cytotoxic Compounds and Inhibitors of Multidrug Resistance by P–glycoprotein"; (1996) *British Journal of Cancer* 74:677–682.

Berger J.G. et al. (1970) "Cycloalkapyrrolones via Decarboxylative Ring Closure of Pyrrole–3–alkanoic Acids and Derivatives" *Journal of Organic Chemistry* 35(9):3122–3126.

Ek, A. and Witkop, B. (1954) "The Synthesis of Labile Hydroxytryptophan Metabolites" *Journal of the American Chemical Society* 76(22):5579–5588.

Furusho, Y. et al. (1996) "Synthesis and optical resolution of axially dissymmetric pyrroles and pyrocolls: new catalysts for the enantioselective addition of diethylzinc to aromatic aldehydes" *Journal of the Chemical Society Perkin Trans. 1* 2:183–190.

Ohno, M. et al. (1990) "Diverse Process in [4+2] Cycloaddition reaction of Silyl Enol Ethers of N–Substituted 2–Acetylpyrroles to an Indole Skeleton" *Tetrahedron Letters* 31(32):4613–4616.

XP–002143293 "4–Ethyl–3–(9'phenanthryl)pyrrole–2, 10'carbolactone" (BRN 7490596) Frankfurt, DE : Beilstein Information systeme GmbH—Retrieved from XFIRE Database.

XP–002143294 "7–oxo–4,5,6, 7–tetrahydro–1H–indole–4–carbonitrile" (BRN 4181226) Frankfurt, DE : Beilstein Information systeme GmbH—Retrieved from XFIRE Database.

XP–002143295 "7–Hydroxy–tryptophan" (BRN 17412) Frankfurt, DE : Beilstein Information systeme GmbH—Retrieved from XFIRE Database.

XP–002143296 "2–ethyl–3–methyl–1,4,5, 6–tetrahydro–indol–7–one" (BRN 1528464) Frankfurt, DE:Beilstein Information systeme GmbH—Retrieved from XFIRE Database.

\* cited by examiner

PREPARATION OF FUSED POLYCYCLIC ALKALOIDS BY RING CLOSURE OF AZOMETHINE YLIDES, NOVEL COMPOUNDS THEREOF AND THEIR USE AS CHEMOTHERAPEUTIC AGENTS

CROSS-REFERENCE TO RELATED APPLICATIONS

This application is a 371 of PCT/AU98/00312, filed May 1, 1998, which takes priority to Australian application PO6565, filed May 2, 1997, both of which are incorporated herein by reference to the extent not inconsistent with the disclosure herewith.

FIELD OF THE INVENTION

The present invention is generally directed to a method for preparing compounds useful in therapy. More particularly, the present invention provides a method for preparing a class of fused polycyclic alkaloids as well as novel compounds obtained thereby, pharmaceutical compositions containing them and methods of treatment using them.

BACKGROUND OF THE INVENTION

Naturally occurring molecules which exhibit potentially beneficial pharmacological properties are isolable from a range of environments, such as marine, plant and microbial sources. One example of such molecules is the general class of compounds known as the Lamellarins. These polyaromatic alkaloids are isolated from marine sources and comprise a fused polyaromatic framework. Lamellarins C and D have been shown to cause inhibition of cell division in a fertilised sea urchin assay, whereas Lamellarins I, K and L all exhibit comparable and significant cytotoxicity against P388 and A549 cell lines in culture. Recently, Lamellarin N has been shown to exhibit activity in lung cancer cell lines by acting as a Type IV microtubule poison. Furthermore, these compounds have also been shown to possess cytotoxic activity on multidrug resistant cells as well as efficacy as non-toxic modulators of the multidrug resistant phenotype and, therefore, afford an attractive potential source of chemotherapeutic agents.

However, the potential clinical usefulness of the Lamellarins is severely limited by the modest quantities produced naturally as well as the difficulties involved in their isolation. Steglich & coworkers, in *Angew. Chem. Int. Ed. Eng.* 1997, 36, 155, have described a biomimetic sequence for the synthesis of Lamellarin G trimethyl ether, however, the process is limited in that it lacks regiochemical control and does not readily lend itself to the specific substitution patterns dictated by the natural products. There is a need, therefore, for a synthetic process which enables the production of the Lamellarins and analogues thereof.

SUMMARY OF THE INVENTION

Throughout this specification, unless the context requires otherwise, the word "comprise", and variations such as "comprises" and "comprising", will be understood to imply the inclusion of a stated integer or group of integers but not the exclusion of any other integer or group of integers.

In a first aspect, the present invention contemplates a method for the preparation of a compound of general Formula (I):

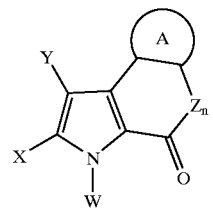

(I)

comprising the step of cyclizing an azomethine ylide of general Formula (II):

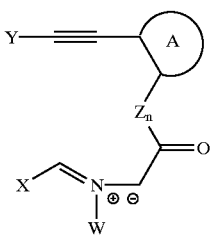

(II)

wherein,

A is a cyclic group being an optionally substituted aryl group or an aromatic heterocyclic group; or A is a cyclic group $R^{A1}R^{A2}C$—$CR^{A3}R^{A4}$ wherein $R^{A2}$ and $R^{A3}$, together with the carbon atoms to which they are attached form an optionally substituted saturated or unsaturated carbocyclic or heterocyclic group and $R^{A1}$ and $R^{A4}$ are as defined below or together form a bond; or A is a non-cyclic group $R^{A1}R^{A2}C$—$CR^{A3}R^{A4}$ wherein $R^{A1}$–$R^{A4}$ are as defined below and $R^{A2}$ and $R^{A3}$ may optionally together form a bond;

Z is a carbon or a heteroatom;

n is selected from 0, 1, 2 or 3; and $R^{A1-A4}$, W, X and Y may be the same or different and each are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, or W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group; or pharmaceutically acceptable derivatives and salts, racemates, isomers and/or tautomers thereof.

Another aspect of the invention contemplates a compound of Formula (I) prepared by the methods as described herein.

Yet another aspect of the invention relates to novel compounds of general Formula (I)

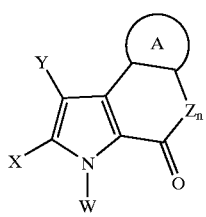

(I)

wherein A, Z, W, X, Y and n are as defined above, provided the compound is not Lamellarin A-N, S-X;

T, U, V or Y 20-sulfate; or D, K, L, M or N-triacetate; G-trimethyl ether; or I-acetate; as herein described.

Still yet another aspect of the present invention relates to a method of treating multidrug resistant tumours comprising the administration of an effective amount of a compound of Formula (I).

A further aspect of the invention provides compositions comprising a compound of Formula (I) together with a pharmaceutically acceptable carrier, excipient or diluent.

DESCRIPTION OF THE PREFERRED EMBODIMENTS

The azomethine ylides of general Formula (II) are obtainable from corresponding precursors by methods known to those skilled in the art, for example as described by A. Padwa et al, in *Chem Rev.*, 1996, 96, (1), 241 and V. P. Litvinov, *Russian Journal of Organic Chemistry*, Vol. 31 (No. 10), 1995, pp. 1301–1340. A particularly suitable means of generating the azomethine ylide of general Formula (II) is effected by the addition of a base to a compound of Formula (III).

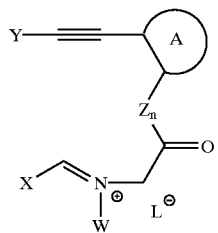

(III)

wherein the counter ion $L^{\ominus}$ is a stable, weakly basic anion.

Suitable anions include those derived from the sulfonates, such as, tosylate, mesylate, triflate, bosylate, besylate, tresylate, nonaflate and nosylate and the halogens, especially chlorine and bromine and iodine. Preferably $L^{\ominus}$ is bromide or iodide.

In a preferred embodiment, the present invention provides a method for the preparation of a compound of Formula (Ia):

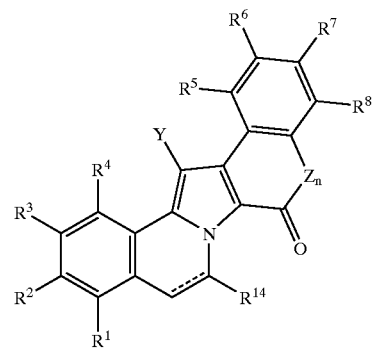

(Ia)

comprising the step of cyclizing an azomethine ylide of general Formula (IIa):

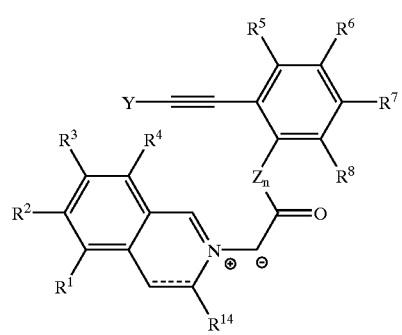

(IIa)

wherein $R^1$–$R^8$ and $R^{14}$ are as defined for W, X and Y as described above.

Preferably, the azomethine ylide of Formula (IIa) is generated by the addition of a base to a compound of general Formula (IIIa):

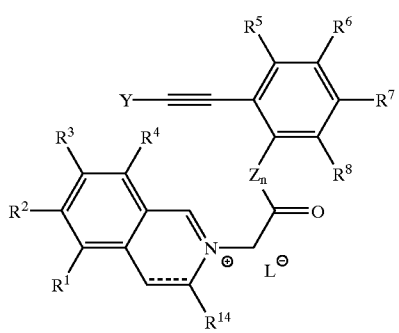

(IIIa)

wherein $R^1$–$R^8$, $R^{14}$, Y, Z, n and $L^{\ominus}$ are as hereinbefore described.

Suitable bases for generating the azomethine ylide of Formula (II) include those derived from alkali metals such as phenyllithium, butyllithium, $KNH_2$ and $NaNH_2$; metal carbonates such as potassium carbonate, lithium carbonate, sodium carbonate and cesium carbonate; as well as amines. In preference, the base used is a mono-, di- or tri-substituted amine, more preferably an alkylamine. Most preferably the base is triethylamine or diisopropylethylamine.

Cyclization of the azomethine ylide may be effected by any suitable means, such as thermal treatment or treatment with metal salts, preferably Cu(I) salts such as CuI. Preferably cyclization is effected by thermal treatment, such as by heating in optionally boiling solvent. Suitable solvents include tetrahydrofuran, chloroform and 1,2-dichloroethane.

In a further preferred aspect, the cyclization of a compound of Formula (II), is followed by oxidative treatment. Oxidative treatment may be performed by means known to and routinely carried out by those skilled in the art. Particularly suitable means include direct oxidation in air, optionally in the presence of silica gel; treatment with Fremy's salt; treatment with quinones such as chloranil or 2,3-dichloro-5,6-dicyano-1,4-benzoquinone (DDQ), and treatment with metal catalysts such as platinum, palladium and nickel. Preferably the oxidative treatment is effected by DDQ or silica gel in air or Fremy's salt. When $L^\ominus$ of compounds of Formula (III) is iodide, oxidation is promoted.

In a preferred embodiment, a compound of general Formula (I) is prepared by treating a compound of general Formula (III) with triethylamine or diisopropylamine followed by thermally induced cyclization and subsequent oxidative treatment with DDQ or silica gel in air. In a more preferred embodiment a compound of general Formula (Ia) is prepared by treating a compound of general Formula (IIIa) with triethylamine or diisopropylamine followed by thermally induced cyclization and subsequent oxidative treatment with DDQ or silica gel in air or Fremy's salt.

When n is 1, Z is preferably selected from one of carbon, nitrogen, oxygen or sulfur. More preferably Z is nitrogen or oxygen. Most preferably, Z is oxygen. When n is 2 or 3, preferably one of Z is carbon, preferably the remaining one is oxygen or nitrogen. Suitable examples where n is 2 or 3 include A-O—$CH_2$—C(O)—, A-$CH_2$—N—C(O)—, A-O—$CH_2$—O—C(O)— and A-$CH_2$—O—$CH_2$—C(O)—.

Preferably, when W and X, together with the nitrogen and carbon atoms to which they are attached, form a saturated or unsaturated heterocyclic group, the group is optionally substituted quinolinyl, optionally substituted isoquinolinyl, optionally substituted dihydroquinolinyl, optionally substituted dihydroisoquinolinyl, optionally substituted pyridyl or dihydro or tetrahydro congeners thereof, or optionally substituted phenanthridine. Preferably, W and X together with the nitrogen and carbon atoms to which they are attached, form an optionally substituted isoquinolinyl or optionally substituted dihydroisoquinolinyl group of general Formula (i):

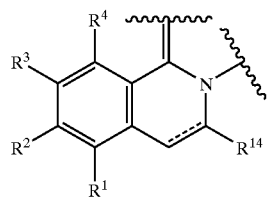

wherein $R^1$–$R^4$ and $R^{14}$ are as defined above.

Preferably $R^1$–$R^4$ are hydrogen, hydroxy, optionally substituted alkyl, optionally substituted alkyloxy, acyloxy, or sulfate. Most preferably they are hydrogen, hydroxy, methoxy, isopropoxy methyl, acetoxy or sulfate. Preferably $R^{14}$ is hydrogen or hydroxy.

When A is an aryl group or an aromatic heterocyclic group, ring A may be an optionally-substituted benzene or naphthalene ring or an optionally substituted aromatic heterocyclic group such as pyridine, furan, pyrrole or thiophene and benzene-fused analogues thereof, for example, quinoline, indole, benzofuran and benzothiophene. Attachment of the bicyclic heterocyclic group may be via the benzene or heterocyclic ring. Preferably A is an optionally substituted benzene. Preferably the substituents are hydrogen, hydroxy, optionally substituted alkyl, optionally substituted alkyloxy, acyloxy, or sulfate. Most preferably they are hydrogen, hydroxy, methoxy, iso-propoxy, methyl, acetoxy or sulfate.

When A is a non-cyclic group $R^{A1}R^{A2}C$—$CR^{A3}R^{A4}$, $R^{A1}$–$R^{A4}$ are preferably independently selected from hydrogen, optionally substituted alkyl, optionally protected hydroxy, optionally substituted alkoxy or acyloxy. Preferably at least one of $R^{A1-A4}$ is hydrogen. More preferably at least two are hydrogen. More preferably at least three are hydrogen. Most preferably all $R^{A1}$–$R^{A4}$ are hydrogen. When $R^{A2}$ and $R^{A3}$ together form a bond so as to form the group $R^{A1}C$=$CR^{A4}$, preferably at least one, or preferably both, of $R^{A1}$ and $R^{A4}$ are hydrogen.

When A is a cyclic group $R^{A1}R^{A2}C$—$CR^{A3}R^{A4}$ as defined above, preferably $R^{A2}$–$R^{A3}$ form a 3 to 8-membered cyclic group, preferably 5 to 6-membered. Preferably, $R^{A2}$ and $R^3$ together with the carbons to which they are attached form a cyclopentane, cyclohexane, cyclopentene, cyclohexene, cyclopentadiene, cyclohexadiene, tetrahydrofuran, dihydrofuran, pyrrolidine, pyrroline, pyran, dihydrophyran, tetrahydropyran or piperidene group. In another preferred form, $R^{A1}$ and $R^{A4}$ are hydrogen.

Preferably Y is an optionally substituted phenyl group of Formula (ii):

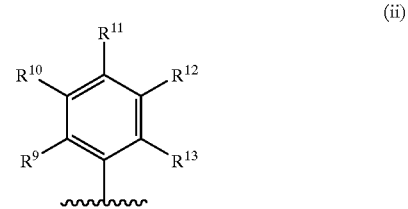

wherein $R^9$–$R^{13}$ are as defined for $R^1$–$R^8$ and $R^{14}$ as described above.

More preferably, $R^9$–$R^{13}$ are hydrogen, hydroxy, optionally substituted alkyl, optionally substituted alkoxy or acyloxy. Most preferably, $R^9$–$R^{13}$ hydrogen, hydroxy, methoxy, iso-propoxy, methyl, acetoxy or sulphate.

The method of the present invention is particularly suitable for the preparation of compounds 1 to 39 as depicted in Tables 1 and 2.

As used herein the term "alkyl", denotes straight chain, branched or cyclic fully saturated hydrocarbon residues. Unless the number of carbon atoms is specified the term preferably refers to $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein the term "alkenyl" denotes groups formed from straight chain, branched or cyclic hydrocarbon residues containing at least one carbon-carbon double bond including ethylenically mono-, di- or poly-unsaturated alkyl or cycloalkyl groups as previously defined. Unless the number of carbon atoms is specified the term preferably refers to $C_{1-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein the term "alkynyl" denotes groups formed from straight chain, branched or cyclic hydrocarbon residues containing at least one carbon-carbon triple bond including ethynically mono-, di- or poly- unsaturated alkyl or cycloalkyl groups as previously defined. Unless the number of carbon atoms is specified the term preferably refers to $C_{1-20}$ alkynyl. Examples include ethynyl, 1-propynyl, 2-propynyl, and butynyl isomers, and pentynyl isomers.

The terms "alkoxy, "alkenoxy and "alkynoxy respectively denote alkyl, alkenyl and alkynyl groups as hereinbefore defined when linked by oxygen.

The term "halogen" denotes fluorine, chlorine, bromine or iodine.

The term "aryl" denotes single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl.

The term "heterocyclic" denotes mono- or polycarbocyclic groups wherein at least one carbon atom is replaced by a heteroatom, preferably selected from nitrogen, sulphur and oxygen. Suitable heterocyclic groups include N-containing heterocyclic groups, such as, unsaturated 3 to 6 membered heteromonocyclic groups containing 1 to 4 nitrogen atoms, for example, pyrrolyl, pyrrolinyl, imidazolyl, imidazolinyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidyl, pyrazolidinyl or piperazinyl;

condensed saturated or unsaturated heterocyclic groups containing 1 to 5 nitrogen atoms, such as, indolyl, isoindolyl, indolinyl, isoindolinyl, indolizinyl, isoindolizinyl, benzimidazolyl, quinolyl, isoquinolyl, indazolyl, benzotriazolyl, purinyl, quinazolinyl, quinoxalinyl, phenanthradinyl, phenathrolinyl, phthalazinyl, naphthyridinyl, cinnolinyl, pteridinyl, perimidinyl or tetrazolopyridazinyl;

saturated 3 to 6-membered heteromonocyclic groups containing 1 to 3 oxygen atoms, such as tetrahydrofuranyl, tetrahydropyranyl, tetrahydrodioxinyl, unsaturated 3 to 6-membered hetermonocyclic group containing an oxygen atom, such as, pyranyl, dioxinyl or furyl;

condensed saturated or unsaturated heterocyclic groups containing 1 to 3 oxygen atoms, such as benzofuranyl, chromenyl or xanthenyl;

unsaturated 3 to 6-membered heteromonocyclic group containing 1 to 2 sulphur atoms, such as, thienyl or dithiolyl;

unsaturated 3 to 6-membered heteromonocyclic group containing 1 to 2 oxygen atoms and 1 to 3 nitrogen atoms, such as, oxazolyl, oxazolinyl, isoxazolyl, furazanyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl, thiazolinyl or thiadiazoyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

The term "acyl" refers to a carboxylic acid residue wherein the OH is replaced with a residue, for example, as defined for W, X, and Y and specifically may denote carbamoyl, aliphatic acyl group or acyl group containing an aromatic ring, which is referred to as aromatic acyl or a heterocyclic ring, which is referred to as heterocyclic acyl, preferably $C_{1-20}$ acyl. Examples of suitable acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and- tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The term "acyloxy" refers to acyl, as herein before defined, when linked by oxygen.

In this specification "optionally substituted" is taken to mean that a group may or may not be further substituted or fused (so as to form a condensed polycyclic group) with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, cyano, nitro, sulfate and phosphate groups.

As used herein, the term "protecting group", refers to an introduced functionality which temporarily renders a particular functional group inactive. The term "protected hydroxy" refers to a hydroxy group which has been temporarily rendered inactive by a protecting group. Suitable protecting groups are known to those skilled in the art, for example as described in *Protective Groups in Organic Synthesis* (T. W. Greene and P. G. M. Wutz, Wiley Interscience, New York).

As used herein, "heteroatom" refers to any atom other than a carbon atom which may be a member of a cyclic organic compound. Examples of suitable heteroatoms include nitrogen, oxygen, sulfur, phosphorous, boron, silicon, arsenic, sellenium and telluruim.

As used herein, the term "base" refers to any proton acceptor/electron pair donator suitable for the generation of an azomethine ylide.

The term "synthon" is taken to refer to a structural or chemical equivalent for a desired functional unit and which can be converted to the desired unit by known or conceivable synthetic operations As used herein, the term "leaving group" refers to a chemical group which is displaced by a nucleophile. Suitable leaving groups include those with the ability to stabilize the negative charge which it carries such as the halogens, sulfates as hereinbefore defined, protonated alcohols and ethers, pyridinium salts, iminium salts such as derived from dicyclohexylcarbodiimide (DCC) and diazonium ions.

The present invention is hereinafter described using a compound of Formula (II) prepared by the hereinafter described methods. This is done, however, with the understanding that the present invention extends to compounds of Formula (II) prepared by any other means.

Accordingly, another aspect of the invention relates to a process for the preparation of a compound of Formula (I) comprising:

a) coupling a compound of Formula (IV) with a compound of Formula (V):

(V)

-continued

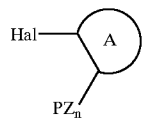
(IV)

to afford the compound of Formula (VI):

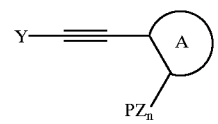
(VI)

wherein $PZ_n$ is a synthon for $Z_n$.

b) unmasking $Z_n$ of compound (VI) and coupling with a compound L-CH$_2$—C(O)-L', to provide compound (VII):

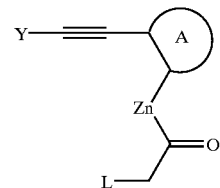
(VII)

wherein L' is a leaving group or a substituent convertible to a leaving group.

c) treatment of compound (VII) with an imine of Formula (VIII)

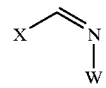
(VIII)

d) generation of the azomethine ylide of general formula (II) and subsequent cyclization of the ylide:

wherein Hal is a halogen and A, L, W, X, Y, Z and n are as hereinbefore described.

In a preferred embodiment, the present invention relates to a process for the preparation of a compound of Formula (Ia) comprising:

(a) coupling a compound of Formula (IV) with a compound of Formula (Va):

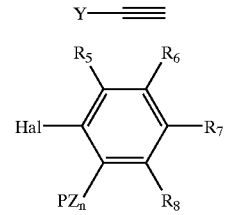
(IV)
(Va)

to afford the compound of Formula (VIa):

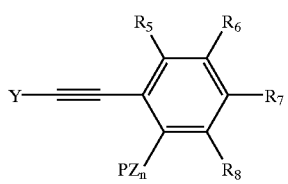

(b) unmasking $Z_n$ of compound (VIa) and coupling with a compound L-CH$_2$—C(O)-L' to provide compound (VIIa):

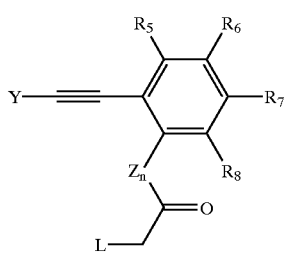

(c) treatment of compound (VIIa) with a compound of Formula (VIIIa):

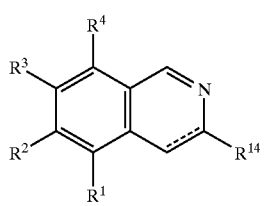

(d) generation of the azomethine ylide of general Formula (IIa) and subsequent cyclization of the ylide;

wherein Hal, L, L', PZ, Y, Z, $R^1$–$R^8$, $R^{14}$ and n are as hereinbefore defined.

Preferably Y is optionally substituted phenyl of Formula (ii). More preferably, Y is phenyl substituted with optionally substituted alkyl, optionally substituted alkoxy or acyloxy. Most preferably, Y is phenyl substituted with hydrogen, hydroxy, methoxy, methyl or acetoxy.

In a preferred aspect, P is a protecting group for $Z_n$ and unmasking $Z_n$ refers to removal of the protecting group. Removal of the protecting group P may be carried out under routine conditions known to those skilled in the art, for example as described in *Protective Groups in Organic Synthesis*. Preferably, P is a protecting group which is labile under hydrolysis conditions. Even more preferably, P is acetyl. In a preferred embodiment, n is 1, Z is oxygen and P is acetyl.

In another preferred aspect, wherein the terminal Z is oxygen, $PZ_n$ is an aldehyde or acyl group. Unmasking of $Z_n$ comprises oxidation, such as Baeyer-Villiger oxidation, of the aldehyde or acyl to a corresponding ester followed by hydrolysis.

Other suitable synthons are known to those skilled in the art.

Preferred L' is halogen, most preferably chlorine or bromine, or OH converted to a leaving group preferably by reaction with DCC.

The coupling of compounds of general Formula (IV) with those of Formula (V) may be suitably carried out under conditions known and routinely employed by those skilled in the art, for example in the presence of catalysts such as Pd(PPh$_3$)$_4$, PdCl$_2$(PPh$_3$)$_2$ or Cu(I) mediated conditions, e.g., CuI, and such as those described by Sonogashira in *Comprehensive Organic Synthesis*, (Ed. B. M. Trost and I. Fleming, Peramon Press, New York, 1991, Vol. 3, 521).

Schemes 1 to 4 provide a schematic overview of representative methods of the invention.

Scheme 1[a]

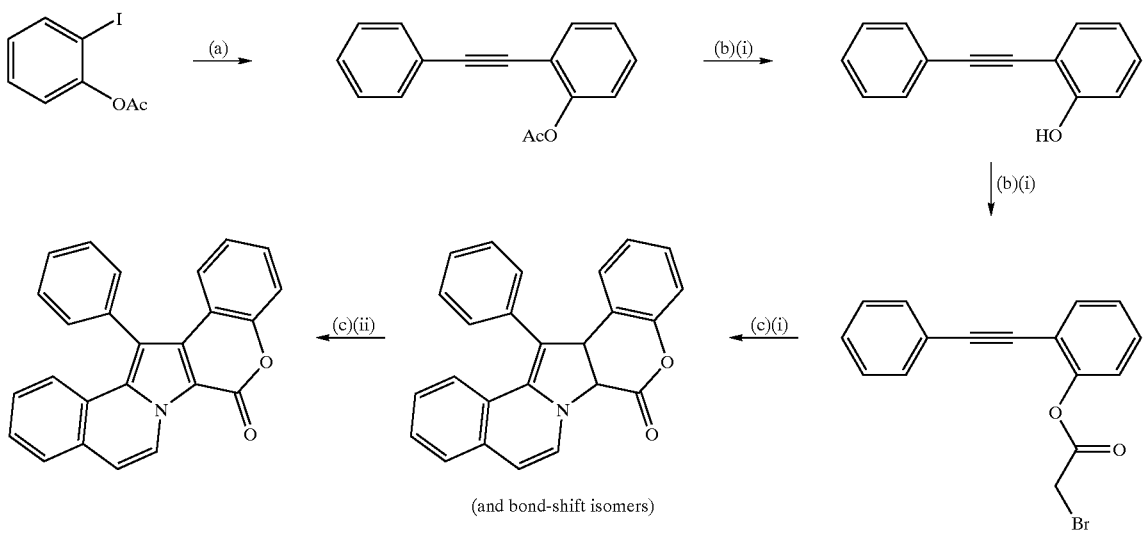

(and bond-shift isomers)

[a]Key: (a) Phenylacetylene 1.1 equiv., Pd(PPh$_3$)$_4$ 0.01%, CuI 0.02%, Et$_3$N, 18° C., 4h.
(b) (i) K$_2$CO$_3$ 1.5 equiv., MeOH, 0.25 h; (ii) 2-bromoacetic acid, 1 equiv., DCC 1.05 equiv., DMAP 0.05 equiv., 18° C., (92)% .
(c) (i) isoquinoline 1 equiv., THF, 18° C., 36h then Et$_3$N 1 equiv., CHCl$_3$, reflux, 8h; (i) DDQ 1 equiv., CH$_2$Cl$_2$, 18° C., 2h (92%).

Scheme 2[a]

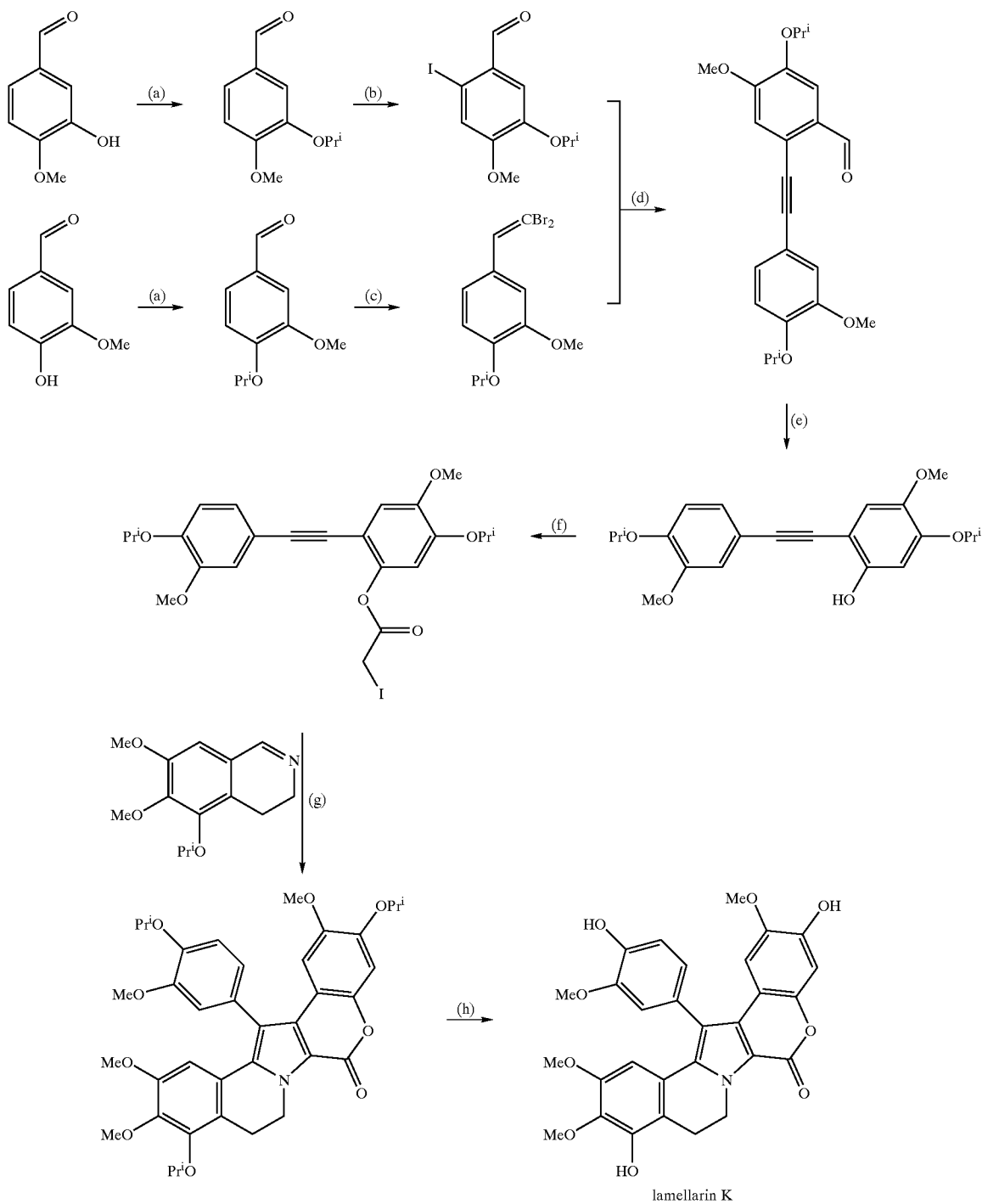

[a]Key: (a) K$_2$CO$_3$ 2 equiv., Pr$^i$Br 1.3 equiv., DMF, 80° C., 13h (100%).
(b) I$_2$ 1.1 equiv., AgO$_2$CCF$_3$ 1.1 equiv., 65° C., 7h (93%).
(c) CBr$_4$ 2 equiv., PPh$_3$ 2 equiv., Zn 2 equiv., (100%).
(d) nBuLi 2 equiv. added to solution of the gemdibromostyrene in THF a t -78° C. then ZnCl$_2$ 1.1 equiv. -78→18° C. then aryliodide 1 equiv., Pd(PP$_3$)$_4$ 0.02 equiv., 18° C. 1.5h (84%).
(e) mCPBA 1.3 equiv., KHCO$_3$ 3 equiv., CH$_2$Cl$_2$ 0→18° C. (92%).
(f) 2-Iodoacetic acid 1.1 equiv., DCC 1.1 equiv., DMAP 0.05 equiv., CH$_2$Cl$_2$, 18° C. 4h (97%).
(g) 3,4-Dihydro-6,7-dimethoxy-5-isopropoxyisoquinoline 1.1 equiv., 1,2-dichoroethane (solvent), 18° C. 8h then Pr$^i_2$NEt 1 equiv., 83° C., 32h (81%).
(h) AlCl$_3$ 3.6 equiv., CH$_2$Cl$_2$, 18° C., 4h (95%).

Scheme 3[a]

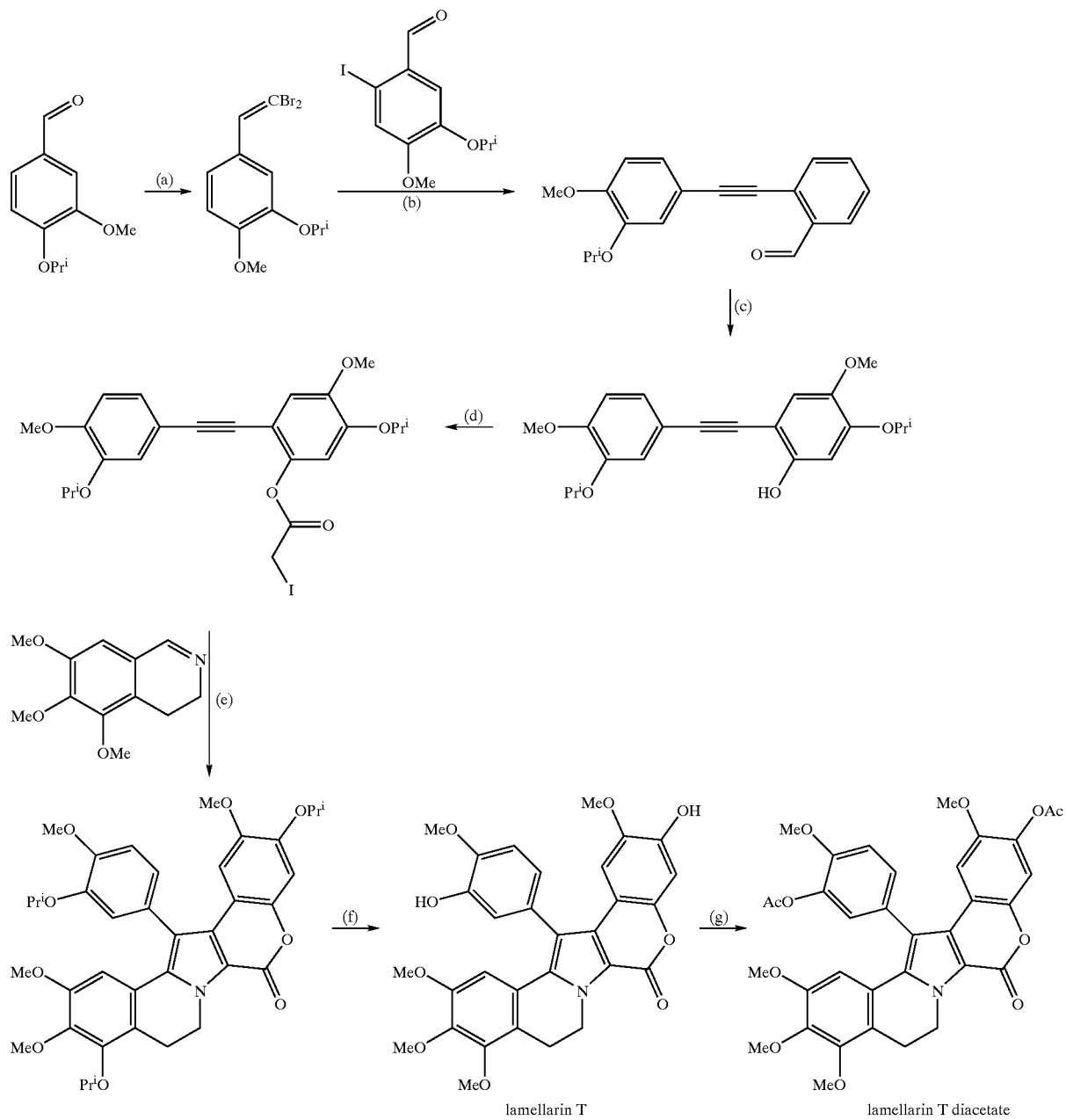

[a]Key: (a) CBr$_4$ 2 equiv., PPh$_3$ 2 equiv., Zn 2 equiv., (100%).
(b) nBuLi 2 equiv., added to solution of the gemdibromostyrene in THF at -78° C. then ZnCl$_2$ 1.1 equiv., -78→18° C. then aryl iodide 1 equiv., PdCl$_2$(PPh$_3$)$_4$ 0.005 equiv., 18° C. 1.5h (92%).
(c) mCPBA 1.2 equiv., KHCO$_3$ 3 equiv., CH$_2$Cl$_2$, 0→18° C. (93%).
(d) 2-Iodoacetic acid 1.05 equiv., DCC 1.05 equiv., DMAP 0.01 equiv., CH$_2$Cl$_2$, 18° C., 4h (94%).
(e) 3,4-Dihydro-5,6,7-trimethoxyisoquinoline 1.2 equiv., 1,2-dichloroethane (solvent), 18° C., 15h then Pr$^i_2$NEt 1 equiv., 24° C., 32h (71%).
(f) AlCl$_3$ 2.4 equiv., CH$_2$Cl$_2$, 18° C., 0.5h (90%).
(g) Ac$_2$O/pyridine (1:1, solvent), DMAP cat., 18° C., 26h (83%).

Scheme 4[a]
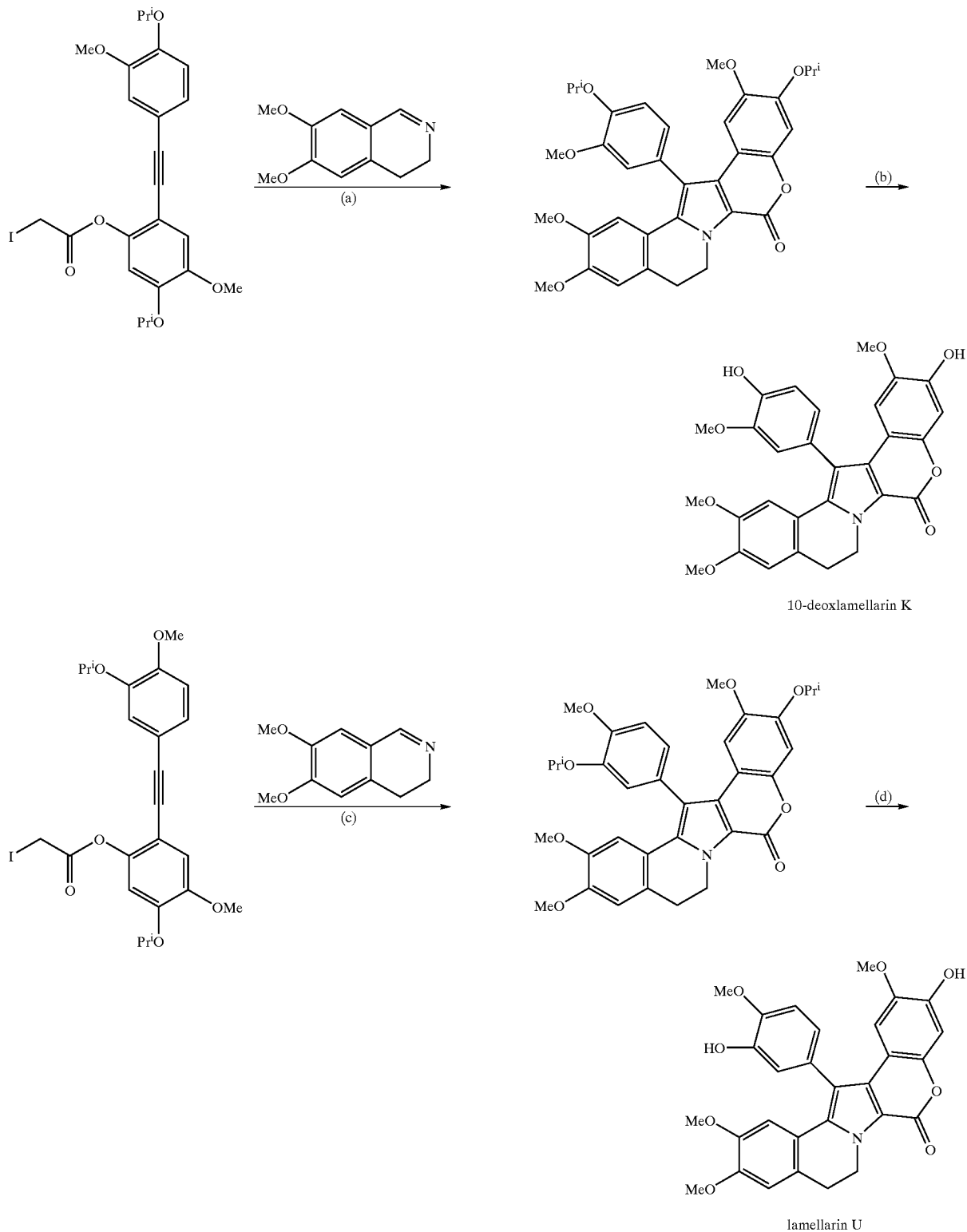
10-deoxlamellarin K
lamellarin U

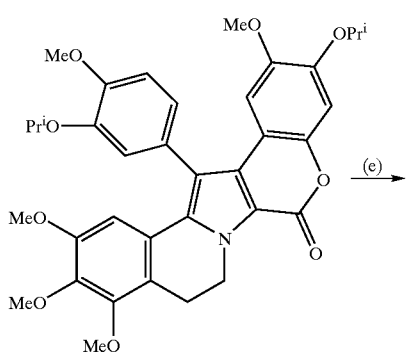
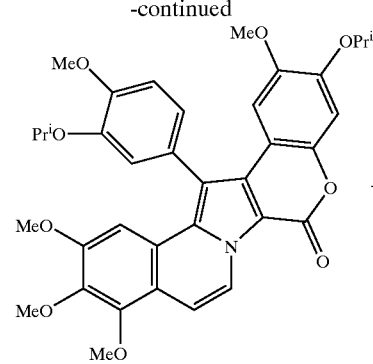
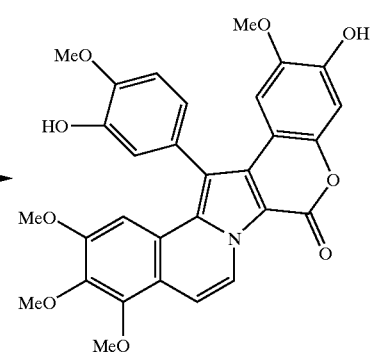

lamellarin W

[a]Key: (a) 3,4-Dihydro-6,7-dimethoxyisoquinoline 1.2 equiv., 1,2-dichloroethane (solvent), 18° C., 15h then Pr$^i_2$NEt 1.05 equiv., 83° C., 28h (79%).
(b) AlCl$_3$ 3 equiv., CH$_2$Cl$_2$, 18° C., 16h (89%).
(c) 3,4-Dihydro-6,7-dimethoxyisoquinoline 1.2 equiv., 1,2-dichloroethane (solvent), 18° C., 17h then Pr$^i_2$NEt 1.05 equiv., 83° C., 20h (70%).
(d) AlCl$_3$ 3.3 equiv., CH$_2$Cl$_2$, 18° C., 14h (94%).
(e) DDQ 1.25 equiv., CHCl$_3$, 65° C., 2h (99%).
(f) AlCl$_3$ 3.3 equiv., CH$_2$Cl$_2$, 18° C., 17h (94%).

The method of the present invention encompasses the synthesis of a large group of compounds. Traditionally, drug candidates are synthesized individually, this being a time consuming and laborious process if the synthetic sequence contains even just a few steps and large numbers of compounds are to be evaluated for their biological activity. Combinatorial synthesis is an emerging technique for effectuating the generation of large libraries of molecules and has been successfully exploited in the synthesis and evaluation of small organic molecule libraries. These libraries may exist as molecules in free solution or linked to a solid phase, for example, polymer beads, pins, microtitre plates or microchips. Chemical diversity can be achieved by either parallel or split (split and mix) syntheses wherein each step has the potential to afford a multitude of compounds. Solution phase libraries may be prepared via parallel syntheses wherein different compounds are synthesised in separate reaction vessels in parallel, often in an automated fashion. Alternatively, attachment of the individual components employed in a synthetic sequence to an appropriate solid phase support allows for the further creation of chemical diversity by utilizing not only parallel synthesis but also split synthesis wherein the solid support containing the compounds prepared in the prior step can be split into a number of batches, treated with the appropriate reagent and recombined. By performing one or more of the steps a)–c), as hereinbefore described, in a parallel or split fashion, in solution phase or on solid support, the present invention is amenable to the generation of large numbers of compounds of general Formula (I).

Accordingly, another aspect of the present invention provides a means for generating compounds of Formula (I) by performing one or more of the following steps:

(a) the coupling of a compound of Formula (IV) with a compound of Formula (V),
(b) unmasking Z$_n$ of the compound of Formula (VI) and coupling with a compound L-CH$_2$—C(O)-L',
(c) treatment of the compound of Formula (VII) with the imine of Formula (VIII), in a parallel or split fashion, in solution phase or on solid support.

Another aspect of the invention contemplates novel compounds of the general Formula (I):

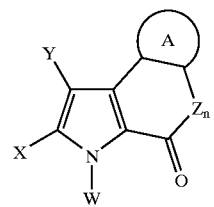

(I)

provided the compound is not Lamellarin A-N, S-X; T, U, V or Y 20-sulfate; or D, K, L, M or N-triacetate; or I-acetate as described in Tables 1 and 2 or G-trimethyl ether;.

A further aspect of the invention contemplates compounds of the general Formula (II):

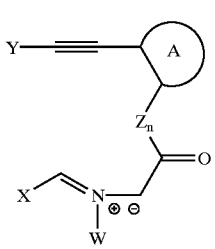

(II)

Yet another aspect of the invention contemplates a compound of general Formula (III):

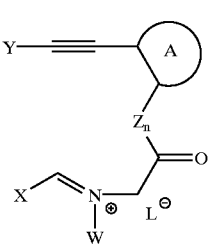

(III)

Another aspect of the invention contemplates the compounds of the general Formula (I) when prepared by the methods herein described.

Yet another aspect of the present invention contemplates a method of treatment comprising the administration of a treatment effective amount of a compound of general Formula (I), as an active ingredient, to an animal, including a human, in need thereof. Preferably the compound of general Formula (I) is prepared by the methods as hereinbefore described.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 10 g per kg of body weight per dosage. Preferably, the dosage is in the range of 1 $\mu$g to 10 g per kg of body weight per dosage. More preferably, the dosage is in the range of 1 mg to 10 g per kg of body weight per dosage. Even more preferably, the dosage is in the range of 1 mg to 5 g per kg of body weight per dosage. More preferably, the dosage is in the range of 1 mg to 2 g per kg of body weight per dosage. More preferably, the dosage is in the range of 1 mg to 1 g per kg of body weight per dosage.

In a preferred embodiment, the method of treatment relates to treating multidrug resistant tumors.

In another embodiment, the method of treatment contemplates improving the antitumor chemotherapeutic effect of multidrug resistant affected drugs.

In another preferred embodiment, the method of treatment is a method for inducing apoptosis. More preferably, the method of treatment is a method of inducing apoptosis on a multidrug resistant cell.

In another embodiment, the method of treatment contemplates modulating immunological functions.

The active ingredient may be administered in a single dose or a series of doses. While it is possible for the active ingredient to be administered alone, it is preferable to present it as a composition, preferably as a pharmaceutical composition.

Yet another aspect of the invention contemplates compositions comprising a compound of general Formula (I) together with a pharmaceutically acceptable carrier, excipient or diluent. Preferably the compound of general Formula (I) is prepared by the methods as hereinbefore described.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylie acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The present invention also provides the use of a compound of general Formula (I) for the manufacture of a medicament for treatment of an animal or human in need thereof. Preferably the compound of general Formula (I) is prepared by the methods as hereinbefore described.

Another aspect of the invention contemplates an agent comprising a compound of general Formula (I) for the treatment of an animal or human in need thereof. Preferably the compound of general Formula (I) is prepared by the methods as hereinbefore described.

In a first embodiment, the agent is for treating multidrug resistant tumors.

In another embodiment the agent is for inducing apoptosis on a multi-drug resistant cell.

In yet another embodiment, the agent is for improving the anti-tumour chemotherapeutic effect of multidrug resistant affected drugs.

A further embodiment is an agent for modulating immunological functions.

Yet another aspect of the invention contemplates the use of a compound of general Formula (I) for the treatment of an animal or human in need thereof. Preferably the compound of general Formula (I) is prepared by the methods as hereinbefore described.

In a preferred embodiment, the use is in the treatment of multidrug resistant tumours.

In a further embodiment, the use is in improving the chemotherapeutic effect of multidrug resistant affected drugs.

Yet another embodiment is the use in modulating immunological functions.

In another embodiment, the invention contemplates the use of a compound of general Formula (I) for inducing apoptosis in an animal or human in need thereof. Preferably apoptosis in a multidrug resistant cell.

The following abbreviations as used in the hereinafter described embodiments of the present invention.

| DCC | Dicyclohexylcarbodiimide |
|---|---|
| DDQ | 2,3-Dichloro-5,6-dycano-1,4-benzoquinone |
| DMAP | 4-(N,N)-dimethylaminopyridine |
| THF | Tetrahydrofuran |

In one embodiment of the invention, Compound 1 was prepared by Sonogashira cross-coupling of phenylacetylene and o-iodophenylacetate to give, after hydrolysis of the initial coupling product, o-hydroxytolan. This last compound was reacted with bromoacetylbromide under standard conditions to deliver the ester which was then treated with isoquinoline to give the isoquinoline salt which was immediately treated with triethylamine (so as to generate the associated azomethine ylide) in refluxing THF and the mixture of dihydropyrrole-type cycloaddition products thereby obtained were subjected to oxidation with either 2,3-dichloro-5,6-dicyano-1,4-benzoquinone (DDQ) or silica gel in air. In his manner, the target Compound 1 was obtained and its structure established by single-crystal X-ray analysis.

In another embodiment, subjection of a more highly oxygenated tolan-ester to reaction with 6,7-dimethoxy-3,4-dihydroisoquinoline under the same conditions as employed in the formation of Compound 1 provided the 8,9-dihydro-congener Compound 34. Deprotection of Compound 34 with $BCl_3$ or $AlCl_3$ then gave Compound 35.

The present invention is now described with reference to the following non-limiting Examples.

EXAMPLE 1

4-Phenyl-6H-[1]Benzopyrano[4',3':4,5]pyrrolo[2,1-a]isoquinolin-6-one (Compound 1)

o-Acetoxytolan: $Pd(PP_3)_4$ (132 mg 0.114 mmol), phenylacetylene (1.3 mL, 1.20 g, 12.6 mmol) and CuI (44 mg, 0.23 mmol) were added, sequentially, to a solution of 2-acetoxyiodobenzene (3.0 g, 11.45 mmol) in $Et_3N$ (20 mL) and the reaction mixture stirred for 4 h at room temperature. The reaction mixture was then concentrated under vacuum at room temperature. The residue was dissolved in $CH_2Cl_2$ (50 mL) and the resulting solution washed with HCl (1×50 ml of a 0.5 M aqueous solution) and brine (1×50 ml) then dried ($MgSO_4$), filtered and concentrated on to silica gel (8 g). This solid was subjected to chromatography (silica gel; 3:1, 2:1, 1:1 then 1:2 hexane/$CH_2Cl_2$ elution) and concentration of the appropriate fractions then gave pure o-acetoxytolan (2.7 g, 100%). Spectra of this compound are identical with those previously reported (A. Arcadi, S. Cacchi, M. D. Rasario, G. Fabrizi and F. Marinelli, *J. Org. Chem.*, 1996, 61, 9280).

o-(α-Bromoacetoxy)tolan: o-Acetoxytolan (2.24 g, 9.50 mmol) was added to a stirring slurry of $K_2CO_3$ (2.0 g, mmol) in methanol (20 mL). After 15 min. the reaction mixture was diluted with HCl (50 ml of a 0.5 M aqueous solution) and extracted with $CH_2Cl_2$ (2×40 mL). The combined extracts were dried ($MgSO_4$) and then concentrated under reduced pressure. The solid residue [pure o-hydroxytolan by $^1H$ nmr] obtained in this manner was dissolved in $CH_2Cl_2$ (20 mL) and α-bromoacetic acid (1.32 g, 9.5 mmol) and DMAP (58 mg, 0.48 mmol) added. Dicyclohexyl carbodiimide (DCC) (2.07 g, 10 mmol) was then added portionwise and the reaction mixture stirred at room temperature for 3 h, then filtered through Celite$^a$ and the filtrate concentrated on to silica gel (8 g). This solid was subjected to flash chromatography on silica gel (sequential elution with 2:1, 1:1 then 1:2 hexane/$CH_2Cl_2$), concentration of the appropriate fractions then gave the title compound ( 2.73 g, 91.2%) as an amber coloured oil. IR(KBr neat, $cm^{-1}$)3060,2221, 1761, 1596, 1571, 1496, 1444, 1258, 1195, 1116, 1099. $^1H$ NMR (300 MHz, $CDCl_3$) δ7.61 (dd, J=1.5, 7.5 Hz, 1H), 7.54–7.52 (m, 2H), 7.41–7.35 (m, 4H), 7.29 (dd, J=1.5, 7.5 Hz, 1H), 7.17 (dd, J=1.4, 8.1 Hz, 1H), 4.13 (s, 2H). $^{13}C$ NMR+APT (75.5 MHz, $CDCl_3$) δ165.0 (C), 150.5 (C), 133.0 (CH), 131.4 (CH), 129.3 (CH), (CH), 128.2 (CH), 126.3 (CH), 122.4 (C), 121.7 (CH), 116.9 (C), 94.6 (C), 83.5 (C), 25.1 ($CH_2$), MS (70 eV) m/z (%): 316 (31) 314 (30) ($M^{+\cdot}$), 193 (100, $M^{+\cdot}$–$COCH_2Br$). Anal. Calcd for $C_{16}H_{11}NO_2Br$: C, 60.98; H, 3.52; Br, 25.35. Found: C, 61.26; H, 3.45; Br, 25.06.

14-Phenyl-6H-[1]benzopyrano[4',3':4,5]pyrrolo[2,1-a]isoqinolin-6-one: Isoquinoline (98 μl, 0.83 mmol) was added to a solution of o-(α-bromoacetoxy)tolan (262 mg, 0.83 mmol) in THF (5 mL) and the resulting mixture allowed to stir at room temperature for 6 h. Addition of $Et_3N$ (215 μl, 0.83 mmol) and chloroform (10 mL) then gave a bright orange solution which was heated at reflux for 4 h at which point a light-yellow solution was achieved. The cooled reaction mixture was concentrated under reduced pressure, the residue dissolved in $CH_2Cl_2$ (7 ml) and DDQ (189 mg, 0.83 mmol) added. The reaction mixture was immediately concentrated on to silica gel (2 g) and subjected to flash chromatography on silica gel (sequential elution with 2:1, 1:1 then 1:2 hexane/$CH_2Cl_2$). Concentration of the appropriate fractions then gave the title compound (277 mg, 92.1%) as white crystalline masses, mp=313–5° C. IR(KBr disc, cm$^{-1}$)3047, 1705, 1536, 1470, 1445, 1411, 1369, 1312, 1179, 1110, 1049. $^1$H NMR (300 MH, CDCl$_3$) δ9.29 (d, J=7.2 Hz, 1H), 7.67 (d, J=7.2 Hz, 1H), 7.64–7.62 (m, 2H), 7.56–7.39 (m, 4H), 7.32 (dt, J=1.8, 7.5 Hz, 1H), 7.25 (dt, J=1.5, 7.5 Hz, 1H), 7.12–7.05 (m, 2H), 6.99 (dt, J=1.5, 7.5 Hz, 1H). $^{13}$C NMR+APT (75.5 MHz, CDCl$_3$) δ155.2 (C), 151.7 (C), 135.6 (C), 134.1 (C), 131.0 (CH), 129.9 (CH), 128.7 (CH), 128.6 (C), 128.4 (CH), 128.1 (CH), 127.5 (CH), 127.3 (CH), 125.0 (C), 124.4 (CH), 124.0 (CH), 123.9 (CH), 117.9 (C), 117.3 (CH), 114.3 (C), 113.4 (CH), 109.3 (CH). MS (70 eV) m/z (%): 361 (100, M$^{+\cdot}$); HRMS calcd for $C_{25}H_{15}NO_2$ 361.1103. Found 361.11031. X-ray obtained.

EXAMPLE 2

Lamellarin K Triisopropylether (Compound 36)

Isovanillin isopropyl ether: Isopropyl bromide (19.0 mL, 200 mmol) was added to a suspension of $K_2CO_3$ (42.0 g, 302 mmol) and isovanillin (23 g, 151.3 mmol) in DMF (100 gmL) and the stirring slurry heated to 80° C. for 13 h. The reaction mixture was then cooled to room temperature, diluted with ether (200 mL) and washed with $H_2O$ (4×200 mL), dried (MgSO$_4$) and concentrated under reduced pressure giving the title compound as a slightly tan oil (29.3 g, 100%) which required no further purification. The spectra of this material are identical with those previously reported (H. Ishii, I.-S. Chen and T. Ishikawa *J. Chem. Soc., Perkin Trans.* 1, 1987, 671.).

Vanillin isopropyl ether: Isopropyl bromide (40.0 mL, 421 mmol) was added to a suspension of $K_2CO_3$ (48.0 g, 348 mmol) and vanillin (40 g, 263 mmol) in DMF (150 mL) and the stirring slurry heated to 80° C. for 15 h. The reaction mixture was then cooled to room temperature, diluted with diethyl ether (200 mL) and washed with $H_2O$ (4×200 mL), dried (MgSO$_4$) and concentrated under reduced pressure giving the title compound as a slightly tan oil (51.0 g, 100%) which required no further purification. The spectra of this material are identical with that previously reported (M. F. Comber and M. V. Sargent, *J. Chem. Soc., Perkin Trans.* 1, 1991, 2783).

2-Iodo5-isopropoxy-4-methoxybenzaldehyde: Silver trifluoroacetate (12.3 g, 56.7 mmol) was added to a solution of isovanillin isopropyl ether (10.0 g, 51.5 mmol) in dry chloroform (120 mL) under nitrogen and the resultant slurry stirred and heated to 61° C. Iodine (14.4 g, 56.7 mmol) was then added portionwise (6 portions) over 0.6 h and the reaction allowed to reflux for a further 6.5 h. The reaction mixture was then cooled and filtered, rinsing with chloroform (50 mL). The filtrate was washed with Na2S$_2$O$_5$ (10% solution in water, 150 mL), NaHCO$_3$ (sat. in water, 150 mL) and water (150 mL) dried (MgSO$_4$) and concentrated under vacuum. The solid residue was suspended in hexane (200 mL) and stirred vigorously for 1 h, cooled in an ice bath for 1 h and filtered rinsing with ice cold hexane (200 mL) to give the title compound as a cream solid (15.3 g, 93%) mp 75–6° C. IR (KBr disc, cm$^{-1}$) 3072, 2978, 2932, 1673, 1581, 1503, 1438, 1385, 1332, 1260, 1215, 1174, 1157, 1133, 1105, 1024, 939. $^1$H NMR 300 MHz, CDCl$_3$) δ9.77 (s, 1H), 7.34 (s, 1H), 7.24 (s, 1H), 4.57 (septet, J=6.0 Hz, 1H), 3.86 (s,3H), 1.31 (d, J=6.0 Hz, 6H). $^{13}$C NMR+APT (75.5 MH, CDCl$_3$) δ194.7(−), 155.5(+), 47.9 (+), 128.2 (+), 122.2 (−), 114.1 (−), 110.8 (+), 92.4 (+), 71.3 (−), 56.4 (−), 21.77 (−), MS (70eV) m/z (%): 320 (M$^{+\cdot}$, 43), 278 (100), 249 (17), 207 (12), 150 (40). Anal. Calcd for $C_{11}H_{13}O_3I$: C, 41.27; H, 4.09; I, 39.64. Found: C, 41.06; H, 3.80; I, 39.59.

β,β-Dibromo-4-isopropoxy-3-methoxystyrene: Carbon tetrabromide (51.3 g, 154.7 mmol) was added portion-wise to a magnetically stirred mixture of zinc dust (0.1 g, 154.5 mmol) and PP$_3$ (40.5 g, 159.4 mmol) in $CH_2Cl_2$ (350 ml) maintained at 0° C. on an ice-salt bath. This suspension was allowed to warm to room temperature and then stirred at for a further 22 h. After this time the reaction mixture was re-cooled to 0° C. and vanillin isopropyl ether (15.0 g, 77.3 mmol) was added dropwise over 2 min. and allowed to stir at room temperature for 1 h. After dilution with hexane (200 ml) the resulting mixture was filtered through a sintered glass funnel and the filtrate concentrated on to silica gel (30 g). The resulting solid was added to the top of a flash chromatography column (silica gel: 20 cm long×10 cm wide) which was subjected to gradient elution (2:1, 1:1 and then 1:2 hexane/$CH_2Cl_2$). Concentration of the appropriate fractions ($R_f$ 0.5 in 1:1 hexane/$CH_2Cl_2$) then afforded the title compound (27.2 g, 99.8%) as white crystalline masses, m.p. 36–38° C. IR(KBr disc, cm$^{-1}$) 2976, 2973, 1599, 1510.1464, 1418, 1383, 1373, 1267, 1235, 1141, 1110, 1036. $^1$H NMR (300 MHz, CDCl$_3$) δ7.41 (s, 1H), 7.21 (d, J=2.1 Hz, 1H), 7.07 (dd, J=2.1, 8.4 Hz, 1H), 6.87 (d, J=8.4 Hz), 4.58 (septet J=6.0 Hz, 1H), 3.87 (s, 3H), 1.39 (d, J=6.0 Hz, 6H). $^{13}$C NMR+APT (75.5 MHz, CDCl$_3$) δ149.7 (C), 147.7 (C), 136.5 (CH), 127.9 (C), 121.9 (CH), 114.4 (CH), 111.8 (CH), 87.1 (CH), 71.1 (CH), 56.0 (CH$_3$), 22.1 (CH$_3$). MS (70 eV) m/z(%): 352 (28), 350 (49), 448 (31) (M$^{+\cdot}$), 310 (51), 308 (100), 306 (54) M$^{+\cdot}$−CH$_2$CHCH$_3$), 295 (34), 293 (38), 291 (36) (M$^{+\cdot}$−CH$_2$CHCH$_3$—CH). Anal. Calcd for $C_{12}H_{14}O_2Br_2$, 41.17; H. 4.03; Br, 45.65. Found: C, 41.21; H, 3.92; Br, 45.47.

2-[(4-Isopropoxy-3-methoxy-phenyl)ethynyl]-5-isopropoxy-4-methoxybenzaldehyde: n-Butyllithium (5.25 mL of a 2.5 M solution in hexane, 13.15 mmol) was added dropwise over 3 mins to a magnetically stirred solution of β,β-dibromo-4-isopropoxy-3-methoxystyrene (2.3 g, 6.58 mmol) in TBF (30 mL) maintained at −78° C. on a dry-ice acetone bath. The slightly tan coloured solution thereby obtained was allowed to stir for a further 50 min at −78° C. then anhydrous ZnCl$_2$ (dried under high vacuum at 120° C. for 20 h) was added to the reaction mixture which slowly became colourless as it was warmed to room temperature over 1 h. Pd(PPh$_3$)$_4$ (145 mg, 0.125 mmol) and aldehyde (2.0 g, 6.26 mmol) were added and the reaction mixture stirred at 18° C. for 4 h. After this time the reaction mix was diluted with ethyl acetate (150 mL) and washed with brine (2×100 ml) then dried (MgSO$_4$), filtered and concentrated on to silica (10 g). The resulting solid was added to the top of a flash chomatography column column (10 cm long×5 cm wide) which was subject to gradient elution (1:1, 1:2, hexane/$CH_2Cl_2$, $CH_2Cl_2$, then 9:1 $CH_2Cl_2$/ethyl acetate). Concentration of the appropriate fractions ($R_f$ 0.4 in $CH_2Cl_2$) then afforded the title compound as white crystalline masses, mp 121–2° C. IR (KBr disc, cm$^{-1}$) 2978, 2933, 2837, 2204, 1687, 1589, 1515, 1509, 1471, 1397, 1357, 1275,1241,1217,1133, 953. $^1$H NMR (300 MHz, CDCl$_3$) δ10.48 (s, 1H), 7.41 (s, 1H), 7.12 (d, J=8.1 Hz, 1H), 7.04 (s, 2 H), 6.87 (d, J=8.1 Hz, 1H), 4.68 (septet, J=6.0 Hz, 1H), 4.58 (septet, J=6.0 Hz, 1H), 3.95 (s, 3H), 3.88 (s, 31), 1.40 (2×d, 2×J=6.0 Hz, 2×6H). $^{13}$C NMR+APT (75.5 MH, CDCl$_3$) δ190.2 (CH), 154.4 (C), 149.7 (C), 148.1 (C), 147.6

(C), 129.6 (C), 124.7 (CH), 121.3 (C), 114.6 (CH), 114.5 (CH), 114.3 (CH), 110.6 (CH), 94.9 (C), 83.4 (C), 71.0 (CH), 70.9 (CH), 56.0 ($CH_3$), 55.7 ($CH_3$), 21.8 ($CH_3$), 21.6 ($CH_3$). MS (70 eV) m/z(%): 382 ($M^{+\cdot}$), 340 (4, $M^{+\cdot}$-$CH_2CHCH_3$), 298 (100, $M^{+\cdot}$-2×$CH_2CHCH_3$), 283 (60, $M^{+\cdot}$-2×$CH_2CHCH_3$—$CH_3$). Anal. Calcd for $C_{23}H_{26}O_5$: C, 72.23; 1H, 6.85. Found: C, 72.08; H, 6.92.

2-[(4-Isopropoxy-3-methoxy-phenyl)ethynyl]-5-isopropoxy-4-methoxyphenol. m-Chloroperoxybenzoic acid [1.2 g, ALDRICH, 50% (remainder 3-chlorobenzoic acid and water), ca. 7.0 mmol] was added in portions over 0.25 h to a magnetically stirred mixture of 2-[(4-isopropoxy-3-methoxy-phenyl)ethynyl]5-isopropoxy-4-methoxybenzaldehyde (2.20 g, 5.75 mmol) and $KHCO_3$ (1.73 g, 17.3 mmol) in $CH_2Cl_2$ (50 mL) maintained at 0° C. (ice-bath). The resulting slurry was stirred for a further 1 h between 0° C. and 18° C. then filtered through Celite® and the solids thus retained rinsed with $CH_2Cl_2$ (1×50 mL). The combined filtrates were concentrated under reduced pressure and the residue treated with NH3 (30 ml of a saturated methanolic solution). After 1 h at 18° C. the reaction mixture was concentrated under reduced pressure and the residue redissolved in $CH_2Cl_2$ (200 mL) then concentrated on to silica gel (8 g, 400–200 mesh). The resulting powder was loaded on top of a column of silica (40-10 mesh TLC grade, 10 cm wide×5 cm long) and eluted with 2:1, 1:1 and 1:2 hexane/$CH_2Cl_2$ then neat $CH_2Cl_2$ (250 ml of each). The appropriate fractions ($R_f$ 0.3 in 1:2 hexane/$CH_2Cl_2$) were concentrated under reduced pressure to give the title compound (1.97 g, 92%) as white crystalline masses, mp 130–1° C. IR(KBr disc, $cm^{-1}$) 3404, 2981,2935, 1620, 1573, 1513, 1467, 1450, 1418, 1383, 1373, 1330, 1269, 1240, 1214, 1166, 1135, 1113, 951. $^1H$ NMR(300 MHz, $CDCl_3$) δ7.03 (dd, J=1.8, 8.4 Hz, 1H), 7.00 (d, J=2.1 Hz, 1H), 6.87 (s, 1H), 6.81 (d, J=8.4 Hz, 1H), 6.53 (s, 1H), 5.81 (s, 1H), 4.52 (septet J=6.0 Hz, 2H), 3.82 (s, 3H), 3.78 (s, 3H), 1.35 (d, J=6.0 Hz, 12H). $^{13}C$ NMR+APT (75.5 MHz, $CDCl_3$) δ151.8 (C), 149.7 (C), 149.3 (C), 147.8 (C), 143.6 (C), 124.6 (CH), 115.0 (C), 114.7 (CH), 114.6 (CH), 114.3 (CH), 102.0 (CH), 100.1 (C), 94.7 (C), 82.2 (C), 71.1 (CH), 71.0 (CH), 56.4 ($CH_3$), 55.7 ($CH_3$), 21.9 ($CH_3$), 21.8 ($CH_3$). MS (70eV) m/z (%): 370 ($M^{+\cdot}$), 355(2, $M^{+\cdot}$-$CH_3$), 328(18, $M^{+\cdot}$-CH($CH_3$)$_2$], 327 (20, $M^{+\cdot}$·$CH_2CHCH_3$), 286 (100, $M^{+\cdot}$-2×$CH_2CHCH_3$), 271 (42, $M^{+\cdot}$-2×$CH_2CHCH_3$—$CH_3$). Anal. Calcd for $C_{22}H_{26}O_5$ C, 71.33; H, 7.07. Found: C, 70.91; H. 7.24.

1-(α-Iodoacetoxy)-2-[(4-isopropoxy-3-methoxy-phenyl)ethynyl]-5-isopropoxy-4-methoxybenzene: DCC (1.60 g, 7.75 mmol) was added to a solution of 2-iodoacetic acid (1.44 g, 7.74 mmol), 2-[(4-sopropoxy-3-methoxy-phenyl)ethynyl]-5-isopropoxy-4-methoxyphenol (2.60 g, 7.03 mmol) and DMAP (43 mg, 0.35 mmol) in $CH_2Cl_2$ (30 mL) and the solution thereby obtained was stirred at 18° C. for 3 h. The resulting suspension was filtered ($CH_2Cl_2$ rinse) and the filtrate concentrated under reduced pressure. The residue was suspended in ether (30 mL) at 0° C. with rapid stirring then filtered [rinsing with $Et_2O$ (20 mL) pre-cooled to 0° C.) giving the title compound(3.67 g, 97%) as a cream solid mp 127–8° C. R (KBr disc, $cm^{-1}$) 2969, 2930, 2833, 1755, 1611, 1575, 1516, 1467, 1416, 1402, 1385, 1365, 1320, 1252, 1236, 1212, 1135, 1108. $^1H$ NMR (300 MHz, $CDCl_3$) δ7.08 (dd, J=1.8, 8.4 Hz, 1H), 7.04 (d, J=2.1 Hz, 1H), 7.01 (s, 1H), 6.82 (d, J=8.4 Hz, 1H), 6.65 (s, 1H), 4.53 (septet, J=6.0 Hz, 2 Hz), 3.95 (s, 2H), 3.85 (s, 6H), 1.38 (d, J=6.0 Hz, 6H), 1.37 (d, J=6.0 Hz, 6H). $^{13}C$ NMR+APT (75.5 MHz, $CDCl_3$) δ167.3 (C), 150.0 (C), 148.4 (C), 148.3 (C), 148.2 (C), 145.1 (C), 125.2 (CH), 115.6 (C), 115.3 (CH), 115.2 (CH), 115.0 (CH), 108.8 (CH), 93.6 (C), 82.7 (C), 72.0 (CH), 71.6 (CH), 56.5 ($CH_3$), 56.3 ($CH_3$), 22.3 ($CH_3$), 22.0 ($CH_3$), -6.2 ($CH_2$). MS (70 eV) m/z (%): 538 (80, $M^{+\cdot}$), 496 (10, $M^{+\cdot}$-$CH_2CHCH_3$), 370 (10, $M^{+\cdot}$-$CH_2ICO$), 328 (34), 286 (100); HRMS calcd for $C_{24}H_{27}O_6I$ 538.0852. Found 538.0854.

Lamellarin K triisopropyl ether: 3,4-Dihydro-6,7-dimethoxy-5-isopropoxyisoquinoline (1.20 g, 4.81 mmol) was added to a solution of 1-(α-iodoacetoxy)-2-[(4-isopropoxy-3-methoxy-phenyl)ethynyl]-5-isopropoxy-4-methoxybenzene (2.30 g mg, 4.27 mmol) in dry 1,2-dichloroethane (40 mL) and the solution stirred at 18° C. for 8 h. After this time diisopropylethylamine (750 μL, 4.30 mmol) was added and the reaction mixture heated at 83° C. for 32 h. The reaction mixture was cooled, evaporated on to silica gel (6 g) and the residue subjected to flash chromatography on silica gel (sequential elution with 2:1:0, 2:3:1 hexane/$CH_2Cl_2$/ether) concentration of the appropriate fractions ($R_f$ 0.4 5:5:2 hexane/$CH_2Cl_2$/ether) giving the title compound (2.28 g, 81%) as a white solid mp 244–5° C. IR(KBr disc, $cm^{-1}$) 2974, 2935, 2832, 1702, 1620, 1539, 1506, 1476, 1465, 1444, 1420, 1259, 1237, 1203, 1175, 1110, 1040. $^1H$ NMR (300 MHz, $CDCl_3$) δ7.10 (m, 2H), 7.05 (s, 1H), 6.92 (s, 1H), 6.64 (s, 1H), 6.60 (s, 1H), 4.74 (br t, J=6.6 Hz, 2H), 4.56 (m, 3H), 3.83 (s, 6H), 3.42 (s, 3H), 3.34 (s, 3H), 3.15 (br t, J=6.6 Hz, 2H), 1.41 (d, J=6.0 Hz, 6H), 1.39 (d, J=6.0 Hz, 6H), 1.31 (d, J=6.0 Hz, 6H). $^{13}C$ NMR+APT (75.5 MHz, $CDCl_3$) δ155.6 (C), 151.7 (C), 151.2 (C), 148.5 (C), 147.0 (C), 146.9 (C), 146.5 (C), 145.9 (C), 142.5 (C), 135.5 (C), 128.5 (C), 128.1 (C), 123.3 (CH), 123.0 (C), 121.1 (C), 116.8 (CH), 115.5 (C), 114.5 (CH), 113.8 (C), 110.3 (C), 104.9 (CH), 104.8 (CH), 104.7 (CH), 103.4 (CH), 75.7 (CH), 71.7 (CH), 71.4 (CH), 60.6 ($CH_3$), 56.1 ($CH_3$), 55.4 ($CH_3$), 55.1 ($CH_3$), 42.3 ($CH_2$), 22.7 ($CH_3$), ($CH_3$). MS (70 eV) m/z (%): 657 (100, $M^{+\cdot}$), 615 (44, $M^{+\cdot}$-$CH_2CHCH_3$), 572 (9, $M^{+\cdot}$-2×$CH_2CHCH_3$); HRMS calcd for $C_{38}H_{43}NO_9$ 657.2938. Found 657.2938.

EXAMPLE 3

Lamellarin K (Compound 21)

Lamellarin K: Aluminium chloride (1.33 g, 9.94 mmol) was added to a solution of lamellarin K triisopropylether (1.80 g, 2.76 mmol) in dry $CH_2Cl_2$ (20 mL) and the reaction allowed to stir for 4 h. After this time the reaction mixture was treated with $NH_4Cl$ (a saturated solution in $H_2O$, 20 mL). The two phases were transferred to a separatory funnel, diluted with ethyl acetate (50 mL) and washed with $H_2O$ (40 mL). The aqueous layer was extracted with ethyl acetate (2×40 mL). The combined organic phases were dried ($MgSO_4$) and concentrated on to silica gel (8 g). The residue was subjected to flash chromatography on silica gel (sequential elution with 20:1, 10:1, 5:1 $CH_2Cl_2$/methanol) the relevant fractions ($R_f$0.6 10:1 $CH_2Cl_2$/methanol) were concentrated giving lamellarin K (1.4 mg, 95%) as white solid, mp 230–2° C. IR (KBr disc, $cm^{-1}$) 3472, 2940,2839, 1709, 1600, 1549, 1511, 1458, 1428, 1407, 1265, 1207, 1142, 1122, 1031. $^1H$ NMR(300 MH, $CDCl_3$) δ7.13 (d, J=8.1 Hz, 1H), 7.07(dd, J=1.5, 8.1 Hz, 1H), 6.97 (s, 1H), 6.96 (d, J-1.5 Hz, 1H), 6.59 (s, 1H), 6.38 (s, 1H), 5.95 (s, 1H), 5.75 (s, 1H), 5.71 (s, 1H), 4.90 (m, 1H), 4.64 (m, 1H), 3.89 (s, 3H), 3.87 (s, 3H), 3.49 (s, 3H), 3.36 (s, 3H), 3.12 (m, 2H). $^1H$ NMR (300 MHz, $d_6DMSO$) δ9.29 (br s, 2H), 7.03 (br s, 1H), 6.99 (dd, J=1.5, 8.1 Hz, 1H), 6.82 (d, J=8.1 Hz, 1H), 6.74 (s, 1H), 6.54 (s, 1H), 6.34 (s, 1H), 4.54 (m, 2H), 3.75 (s, 3H), 3.55 (s, 3H), 3.35 (s, 3H), 3.27 (s, 3H), 3.01 (m, 2H). $^{13}C$ NMR+APT (75.5 MHz, $d_6DMSO$) δ154.6 (C), 151.0 (C), 148.7 (C), 147.5 (C), 147.0 (C), 146.7 (C), 145.9 (C), 144.6 (C), 136.6 (C), 135.5 (C), 127.8 (C), 125.8 (C), 123.6 (CH), 122.7 (C), 116.5(CH), 115.7 (C), 114.9(CH), 114.5 (C), 112.8 (C), 108.9 (C), 105.2(CH), 103.8 (CH), 101.1 (CH) 60.5 ($CH_3$), 56.2 ($CH_3$), 55.2 ($CH_3$), 54.8 ($CH_3$), 41.9 ($CH_2$), 21.5 ($CH_2$). MS (70 eV) m/z (%): 531 (100, $M^{+\cdot}$), 516 (17, $M^{+\cdot}-CH_3$), 265.5 (4, $M^{2+}$); HRMS calcd for $C_{29}H_{25}NO_9$ 531.1539. Found 531.1524.

EXAMPLE 4

Lamellarin T diisopropyl ether (Compound 37)

β,β-Dibromo-3-isopropoxy-4-methoxystyrene: Carbon tetrabromide (51.3 g, 154.7 mmol) was added portion-wise to a magnetically stirred mixture of zinc dust (10.1 g, 154.5 mmol) and $PP_3$ (40.5 g, 154.4 mmol) in $CH_2Cl_2$ (350 mL) maintained at 0° C. on an ice-salt bath. The resulting suspension was allowed to warm to room temperature and then stirred for a further 22 h. After this time the reaction mixture was re-cooled to 0° C. and isovanillin isopropyl ether (15.0 g, 77.3 mmol) was added dropwise over 2 min. The resulting mixture was allowed to stir at room temperature for 1 h then diluted with hexane (200 mL) and filtered through a No. 3 porosity sintered-glass funnel. The filtrate was concentrated on to silica gel (400–200 mesh, 30 g) and the resulting solid added to the top of a flash chromatography column (20 cm long×10 cm wide) which was subjected to gradient elution with 2:1, 1:1 then 1:2 hexane/$CH_2Cl_2$. Concentration of the appropriate fractions ($R_f$ 0.5 in 1:1 hexane/$CH_2Cl_2$) afforded the title compound (27.0 g, 99%) as white crystalline masses, m.p. 67–69° C. $v_{max}$ (KBr) 3009, 2975, 2929, 1597, 1572, 1508, 1463, 1441, 1429, 1373, 1301, 1276, 1260, 1233, 1144, 1110 and 999 $cm^{-1}$. $^1H$ n.m.r. δ7.38 (s, 1H), 7.24 (d, J=2.1 Hz, 1H), 7.08 (dd, J=8.4 and 2.1 Hz, 1H), 6.84 (d, J=8.4 Hz, 1H), 4.53 (septet, J=6.0 Hz, 1H), 3.86 (s, 3H), 1.38 (d, J=6.0 Hz, 6H). $^{13}C$ n.m.r. δ150.5 (C), 146.7(C), 136.4 (CH), 127.7(C), 122.1 (CH), 115.3 (CH), 111.3 (CH), 87.0(C), 71.4 (CH), 55.8 ($CH_3$), 22.0 (2×$CH_3$). Mass spectrum m/z 352 (20) 350 (40) 348 (22)($M^{+\cdot}$), 310 (50) 308 (100) 306 (50) [$(M-C_3H_6)^{+\cdot}$], 295 (30), 293 (61) 291 (33) [$(M-C_3H_6-CH_3^{+\cdot})^+$]. Anal. Calcd for $C_{12}H_{14}Br_2O_2$ C, 41.2; H, 4.0; Br, 45.7. Found: C, 41.1; H, 3.7: Br, 45.3%.

2-[(3-Isopropoxy-4-methoxy-phenyl)ethynyl]-5-isopropoxy-4-methoxybenzaldehyde: n-Butyllithium (45.8 ml of a 2.5 M solution in hexane, 114.5 mmol) was added dropwise over 0.2 h to a magnetically stirred solution of β,β-dibromo-3-isopropoxy4-methoxystyrene (20.0 g, 57.2 mmol) in THF (250 mL) maintained at −78° C. on a dry-ice acetone bath. The slightly tan coloured solution thereby obtained was stirred at −78° C. for 0.5 h then the reaction vessel was removed from the cooling bath. After 0.1 h anhydrous $ZnCl_2$ (7.79 g, 57.2 mmol dried at 120° C. and 0.01 mm Hg for 20 h) was added to the reaction mixture which slowly became colourless as it was warmed to room temperature over 1 h. Aldehyde (17.8 g, 55.6 mmol) then $PdCl_2(PPh_3)_2$ (195 mg, 0.128 mmol) were added and the reaction mixture stirred at 18° C. for 6 h. After this time the reaction mixture was diluted with ethyl acetate (600 mL) and washed with water (2×500 mL) then dried ($MgSO_4$), filtered and concentrated under reduced pressure. The solid thereby obtained was suspended in ether/hexane (100 ml of a 4:1 v/v mixture) and the resulting suspension was subjected to vacuum filtration and the solid thus retained was washed with ether/hexane (2×50 ml of a 4:1 v/v mixture) to afford the title compound (16.5 g, 78%) as white crystalline masses, mp=110–113° C. Subjection of the combined filtrates to flash chomatography (silica, 1:1, 1:2 hexane/$CH_2Cl_2$, $CH_2Cl_2$ and then $CH_2Cl_2$ gradient elution). Concentration of the appropriate fractions ($R_f$ 0.4 in $CH_2Cl_2$) then afforded additional quantities of product (3.64 g, 14%), mp=110–113° C.; $v_{max}$ (KBr) 2978, 2933, 2837, 2203, 1685, 1589, 1515, 1508, 1448, 1397, 1387, 1376, 1358, 1322, 1276, 1240, 1216, 1156, 1132 and 1091 $cm^{-1}$. $^1H$ n.m.r. δ10.49 (s, 1H), 7.41 (s, 1H), 7.21 (dd, J=8.4 and 2.4 Hz, 1H), 7.06 (d, J=2.4 Hz, 1H), 7.03 (s, 1H), 6.84 (d, J=8.4 Hz, 1H), 4.70 (septet, J=6.0 Hz, 1H), 4.57 (septet, J=6.0 Hz, 1H), 3.97 (s, 3H), 3.88 (s, 3H), 1.40 (2×d, J=6.0 Hz,2×6H); $^{13}C$ n.m.r. δ190.5 (CH), 154.5(C), 151.2(C), 147.8(C), 146.9 (C), 129.7 (C), 125.2 (CH), 121.5 (C), 118.2 (CH), 114.4 (CH), 111.7 (CH), 110.7 (CH), 95.0 (C), 83.4 (C), 71.4 (CH), 71.1 (CH), 56.1 ($CH_3$), 55.8 ($CH_3$), 21.9 ($CH_3$), 21.8 ($CH_3$); Mass spectrum m/z 382 (31%, $M^{+\cdot}$), 298 [100, (M−2×$H_2CCHCH_3$)$^{+\cdot}$], 283 [46, (M−2×$H_2CCHCH_3$, —$CH_3$)$^{+\cdot}$]. HRMS, Calcd for $C_{23}H_{26}O_5$ 382.1780. Found 382.1781.

2-[(3-Isopropoxy-4-methoxy-phenyl)ethynyl]-5-isopropoxy-4-methoxyphenol. m-Chloroperoxybenzoic acid [19.4 g, ALDRICH, 50% (remainder 3-chlorobenzoic acid and water), ca. 56 mmol] was added in portions over 0.25 h to a magnetically stirred mixture of 2-[(3-isopropoxy-4-methoxy-phenyl)ethynyl]-5-isopropoxy-4-methoxybenzaldehyde (18.0 g, 47.1 mmol) and $KHCO_3$ (14.1 g, 141.0 mmol) in $CH_2Cl_2$ (220 ml) maintained at 0° C. (ice-bath). The resulting slurry was stirred for a further 1 h between 0° C. and 18° C. then filtered through Celite® and the solids thus retained rinsed with $CH_2Cl_2$ (1×200 mL). The combined filtrates were concentrated under reduced pressure and the residue treated with $NH_3$ (1×300 mL of a saturated methanolic solution). After 1 h at 18° C. the reaction mixture was concentrated under reduced pressure and the residue redissolved in $CH_2Cl_2$ (200 ml) then concentrated on to silica gel (20 g, 400–200 mesh). The resulting powder was loaded on top of a column of silica (40–10 mesh TLC grade, 10 cm wide×5 cm long) and eluted with 2:1, 1:1 and 1:2 hexane/$CH_2Cl_2$ then neat $CH_2Cl_2$ (250 mL of each). The appropriate fractions ($R_f$ 0.3 in 1:2 hexane/$CH_2Cl_2$) were concentrated under reduced pressure to give the title compound (5) (16.2 g, 93%) as white crystalline masses, m.p. 139–140° C. $v_{max}$ (KBr) 3431, 2983, 2934, 1513, 1461, 1332, 1267, 1241, 1210, 1136, 1110, 1024 and 991 $cm^{-1}$. $^1H$ n.m.r. δ7.12 (dd, J=8.1 and 2.1 Hz, 1H), 7.10 (d, J=2.1 Hz, 1H), 6.88 (s, 1H), 6.84 (d, J=8.1 Hz, 1H), 6.56 (s, 1H), 5.61 (s, 1H), 4.55 (septet, J=6.0 Hz, 2×1H), 3.88 (s, 3H), 3.82 (s, 3H), 1.38 (2×d, J=6.0 Hz, 2×6H). $^{13}C$ n.m.r. δ151.8 (C), 151.1 (C), 149.6 (C), 147.0 (C), 143.9 (C), 125.1 (CH), 118.4 (CH), 114.8(C), 114.2 (CH), 111.7 (CH), 101.9 (CH), 100.0 (C), 95.2 (C), 81.8 (C), 71.6 (CH), 71.2 (CH), 56.7 ($CH_3$), 56.0 ($CH_3$), 22.1 ($CH_3$), 21.9 ($CH_3$). Mass spectrum m/z 370 (68, $M^{+\cdot}$), 328 [24, (M−$H_2CCHCH_3$)$^{+\cdot}$], 286 [70, (M−2×$H_2CCHCH_3$)$^{+\cdot}$], 271 [100, (M−2×$H_2CCHCH_3$—$CH_3$)$^+$]. Anal. Calcd for $C_{22}H_{26}O_5$. C, 71.3, H, 7.1. Found: C, 71.5,H,7.1.

1-(α-Iodoacetoxy)-2-[(3-isopropoxy-4-methoxy-phenyl)ethynyl]-5-isopropoxy-4-methoxybenzene: DCC (6.43 g, 31.1 mmol) was added to a solution of 2-iodoacetic acid (5.80 g, 31.2 mmol), 2-[(3-isopropoxy-4-methoxy-phenyl)ethynyl]-5-isopropoxy-4-methoxyphenol (11.0 g, 29.7 mmol) and DMAP (36 mg, 0.30 mmol) in $CH_2Cl_2$ (200 mL) and the solution thereby obtained was stirred at 18° C. for 3 h. The resulting suspension was filtered ($CH_2Cl_2$, 100 mL rinse) and the filtrate concentrated under reduced pressure. The residue thus obtained was suspended in ether (150 mL) at 0° C. with rapid stirring for 2 h then filtered [rinsing with $Et_2O$ (70 mL) pre-cooled to 0° C.] giving the product (15.0 g, 94%) as a cream solid mp 136–7° C. IR(KBr disc, $cm^{-1}$)3021, 2978, 2930, 1771, 1607, 1512, 1460, 1444, 1420, 1330, 1241, 1211, 1133, 1110, 1096. $^1H$ NMR (300 MHz, $CDCl_3$) δ7.12 (dd, J=1.8, 8.4 Hz, 1H), 7.06 (d, J=2.1 Hz, 1H), 7.02 (s, 1H), 6.82 (d, J=8.4 Hz, 1H), 6.66 (s, 1H), 4.55 (septet, J=6.0 Hz, 2 Hz), 3.96 (s, 2H), 3.87 (s, 6H), 1.40 (d, J=6.0 Hz, 6H), 1.38 (d, J=6.0 Hz, 6H). $^{13}C$ NMR+APT (75.5 MHz, CDCl$_3$) δ166.9 (C), 150.8 (C), 147.9(C), 147.8 (C), 146.7 (C), 144.6 (C), 125.1 (CH), 118.3 (CH), 115.0 (C), 114.7 (CH), 111.5 (CH), 108.3 (CH); 93.2 (C), 82.3 (C), 71.5 (CH), 71.3 (CH), 56.1 (CH$_3$), 55.7 (CH$_3$), 22.0 (CH$_3$), 21.8 (CH$_3$), −6.6 (CH$_2$). MS (70 eV) m/z (%): 538 (100 M$^{+\bullet}$), 496 (12, M$^{+\bullet}$−CH$_2$CHCH$_3$), 370 (26, M$^{+\bullet}$−CH$_2$ICO), 328 (62), 286 (81); HRMS calcd for C$_{24}$H$_{27}$O$_6$I 538.0852. Found 538.0843.

Lamellarin T diisopropylether: 3,4-Dihydro-5,6,7-trimethoxyisoquinoline (986 mg, 4.46 mmol) was added to a solution of 1-(α-iodoacetoxy)-2-[(3-isopropoxy-4-methoxy-phenyl)ethynyl]-5-isopropoxy4-methoxybenzene (2.0 g, 3.71 mmol) in dry 1,2-dichloroethane (50.0 mL) and the solution stirred at 18° C. for 15 h. After this time diisopropylethylamine (677 μL, 3.90 mmol) was added and the reaction mixture heated at 83° C. for 24 h. The reaction mixture was cooled, evaporated on to silica gel (5 g) and the residue subjected to flash chromatography on silica gel (elution with 9:1, 6:1 CH$_2$Cl$_2$/ether) concentration of the appropriate fractions (R$_f$ 0.5 7:1 CH$_2$Cl$_2$/ether) giving the title compound(1.67 g, 71%) as a white solid, mp 192–5° C. IR (KBr disc, cm$^{-1}$) 2975, 2935, 2834, 1700, 1620, 1540, 1506, 1476, 1455, 1442, 1416, 1259, 1239, 1208, 1175, 1137, 1116, 1084, 1037, 1013. $^1$H NMR (300 MHz, CDCl$_3$) δ7.07 (brs, 2H), 7.03 (s, 1H), 6.89 (s, 1H), 6.63 (s, 1H), 6.56 (s, 1H), 4.74 (br t, J=6.6 Hz, 2H), 4.52 (m, 2H), 3.92 (s, 3H), 3.88 (s, 3H), 3.85 (s, 3H), 3.42 (s, 3H), 3.33 (s, 3H), 3.12 (br t, J=6.6 Hz, 2H), 1.36 (d, J=6.0 Hz, 6H), 1.32 (d, J=6.0 Hz, 6H). $^{13}$C NMR+APT (75.5 MHz, CDCl$_3$) δ155.6 (C), 151.8 (C), 150.6 (C), 150.0 (C), 148.0 (C), 147.0 (C), 146.5 (C), 145.9 (C), 142.1 (C), 135.3 (C), 128.1 (C), 127.8 (C), 123.6 (CH), 123.0 (C), 120.0 (C), 117.7 (CH), 115.5 (C), 113.8 (C), 112.6 (CH), 110.3 (C), 105.1 (CH), 104.8 (CH), 103.3 (CH), 71.3 (CH), 71.2 (CH), 61.0 (CH$_3$), 60.5 (CH$_3$), 56.3 (CH$_3$), 55.4 (CH$_3$), 55.1 (CH$_3$), 42.1 (CH$_2$), 22.0 (CH$_3$), 21.9 (CH$_2$), 21.8 (CH$_3$). MS (70 eV) m/z (%): 629 (100, M$^{+\bullet}$), 587 (63, M$^{+\bullet}$−CH$_2$CHCH$_3$); HRMS calcd for C$_{36}$H$_{36}$NO$_9$ 629.2625. Found 629.2642.

EXAMPLE 5

Lamellarin T (Compound 26)

Lamellarin T: Aluminium chloride (480 mg, 3.60 mmol) was added to a solution of lamellarin T diisopropylether (945 mg, 1.50 mmol) in dry CH$_2$Cl$_2$ (10.0 mL) and the reaction allowed to stir for 0.5 h. After this time the reaction mixture was treated with NH4Cl (a saturated solution in H$_2$O, 5 mL). The two phases were transferred to a separatory funnel, diluted with H$_2$O (100 mL) and extracted with ethyl acetate (3×100 mL). The combined organic phases were dried (MgSO$_4$) and concentrated on to silica gel (4 g). The residue was subjected to flash chromatography on silica gel (sequential elution with 99:1, 20:1 CH$_2$Cl$_2$/methanol) the relevant fractions (R$_f$ 0.2 20:1 CH$_2$Cl$_2$/methanol) were concentrated giving lamellarin T (736.8 mg, 90%) as white solid, mp 283–4° C. IR (KBr disc, cm$^{-1}$) 3492, 3303, 2998, 2982, 2835, 1677, 1624, 1582, 1551, 1507, 1476, 1462, 1450, 1413, 1273, 1249, 1207, 1160, 1122, 1041, 1023. $^1$H NMR (300 MHz, d$_6$DMSO) δ9.65 (s, 1H), 9.29 (s, 1H), 7.13 (d, J=8.7 Hz, 1H), 6.90 (m, 2H), 6.80 (s, 1H), 6.65 (s, 1H), 6.60 (s, 1H), 4.65 (m, 1H), 4.56 (m, 1H), 3.83 (s, 3H), 3.79 (s, 3H), 3.75 (s, 3H), 3.38 (s, 3H), 3.30 (s, 3H), 3.06 (br t, J=7.0 Hz, 2H). $^{13}$C NMR+APT (75.5 MH, d$_6$DMSO) δ154.3 (C), 151.3 (C), 150.2 (C), 147.7 (C), 147.5 (C), 146.8 (C), 145.6 (C), 144.4 (C), 141.8 (C), 134.5 (C), 127.3 (C), 127.1 (C), 122.4 (C), 121.5 (CH), 120.0 (C), 117.7 (CH), 115.2 (C), 113.3 (CH), 112.8 (C), 108.5 (C), 105.1 (CH), 104.9 (CH), 103.6 (CH), 60.8 (CH$_3$), 60.5 (CH$_3$), 56.0 (CH$_3$), 55.0 (CH$_3$), 54.7 (CH$_3$), 41.6 (CH$_2$), 21.4 (CH$_2$). MS (70 eV) m/z (%): 545 (100, M$^{+\bullet}$), 530 (31, M$^{+\bullet}$−CH$_3$) 272.5 (27, M$^{2+}$); HRMS calcd for C$_{30}$H$_{21}$NO$_9$ 545.1686. Found 545.1690.

EXAMPLE 6

Lamellarin T diacetate (Compound 39)

Lamellarin T diacetate: Lamellarin T (48 mg, 0.088 mmol) was dissolved in a solution of acetic anhydride (1.0 mL) and pyridine (1.0 mL) containing DMAP (several crystals) and the solution stirred at 18° C. for 26 h. The solution was then diluted with ethyl acetate (15 mL) and washed with NaHCO$_3$ (a saturated solution in H$_2$O, 20 mL) and citric acid (10% in H$_2$O, 20 mL) dried over (MgSO$_4$) and concentrated under reduced pressure. The residue was subjected to flash chromatography on silica gel (sequential elution with 2:1, 1:1 hexane/ethyl acetate) the relevant fractions (R$_f$ 0.42 1:1 hexane/ethyl acetate) were concentrated giving the title compound (47 mg, 83%) as a white solid mp 251–2° C. IR (KBr disc, cm$^{-1}$) 2937, 2840, 1769, 1718, 1603, 1545, 1507, 1475, 1456, 1414, 1295, 1266, 1201, 1141, 1117, 1036. $^1$H NMR (300 MHz, CDCl$_3$) δ7.31 (dd, J=2.1, 8.4 Hz, 1H), 7.22 (d, J=2.1 Hz, 1H), 7.14 (d, J=8.7 Hz, 11H), 7.07 (s, 11), 4.90 (m, 1H), 4.60 (m, 1H), 3.90 (s, 3H), 3.89 (s, 3H), 3.45 (s, 3H), 3.39 (s, 3H), 3.13 (m, 2H), 2.30 (s, 6H). $^{13}$C NMR+APT (75.5 MHz, CDCl$_3$) δ168.7 (C), 168.4 (C), 155.0 (C), 151.9 (C), 147.5 (C), 144.8 (C), 142.2 (C), 140.6 (C), 138.7 (C), 135.6 (C), 129.5 (CH), 127.6 (C), 127.2 (C), 125.4 (CH), 122.6 (C), 119.8 (C), 116.1 (C), 114.8 (C), 114.4 (C), 112.9 (CH), 111.7 (CH), 105.4 (CH), 105.0 (CH), 60.9 (CH$_3$), 60.8 (CH$_3$), 56.2 (CH$_3$), 55.5 (CH$_3$), 55.2 (CH$_3$), 42.1 (CH$_2$), 21.7 (CH$_2$), 20.4 (CH$_3$). MS (70 eV) m/z (%): 629 (53, M$^{+\bullet}$), 587 (100, M$^{\bullet}$−CH$_2$CO); HRMS calcd for C$_{34}$H$_3$, NO$_{11}$ 629.1897. Found 629.1907.

EXAMPLE 7

10-Deoxylamellarin K diisopropylether (Compound 34)

10-Deoxylamellarin K diisopropylether: 3,4-Dihydro-6,7-dimethoxyisoquinoline (170 mg, 0.82 mmol) was added to a solution of 1-(a-iodoacetoxy)-2-[(4-isopropoxy-3-methoxy-phenyl)ethynyl]-5-isopropoxy-4-methoxybenzene (400 mg, 0.74 mmol) in dry 1,2-dichloroethane (4.0 mL) and the solution stirred at 18° C. for 5 h. After this time diisopropylethylamine (136 μL, 0.78 mmol) was added and the reaction mixture heated at 83° C. for 28 h. The reaction mixture was cooled, evaporated on to silica gel (3 g) and the residue subjected to flash chromatography on silica gel (sequential elution with 1:2:0, 3:6:1, 0:5:1 hexane/CH$_2$Cl$_2$/ether) concentration of the appropriate fractions (R$_f$ 0.7 9:1 CH$_2$Cl$_2$/ether) giving the title compound (352 mg, 79%) as a white solid, mp 222–3° C. IR (KBr disc, cm$^{-1}$) 2975, 2933, 2831, 1709, 1611, 1578, 1543, 1514, 1485, 1464, 1438, 1415, 1271, 1240, 1212, 1165, 1042. $^1$H NMR (300 MHz, CDCl$_3$) δ7.11 (m, 2H), 7.05 (s, 1H), 6.92 (s, 1H), 6.77 (s, 1H), 6.75 (s, 1H), 6.68 (s, 1H), 4.80 (m, 2H), 4.57 (m, 2H), 3.90 (s, 3H), 3.83 (s, 3H), 3.43 (s, 3H), 3.37 (s, 3H), 3.12 (br t, J=7.0 Hz, 2H), 1.41 (d, J=6.0 Hz, 6H), 1.39 (d, J=6.0 Hz, 6H). $^{13}$C NMR+APT (75.5 MHz, CDCl$_3$) 5 155.5 (C), 151.2 (C), 148.9 (C), 147.4 (C), 147.0 (C), 146.9 (C), 146.5 (C), 146.0 (C), 135.9 (C), 128.5 (C), 128.3 (C), 126.6 (C), 123.4 (CH), 120.1 (C), 116.8 (CH), 114.9 (C), 114.5 (C), 113.7 (C), 110.9 (CH), 110.3 (C), 108.6 (CH), 104.8 (CH), 103.4 (CH), 71.7 (CH), 71.4 (CH), 56.2 (CH$_3$), 55.9 (CH$_3$), 55.5 (CH$_3$), 55.1 (CH$_3$), 42.4 (CH$_2$), 28.7 (CH$_2$), 21.9 (CH$_3$), 21.8 (CH$_3$). MS (70 eV) m/z (%): 599 (100, M$^{+\bullet}$), 557 (61, M$^{+\bullet}$−CH$_2$CHCH$_3$), 515 (49, M$^{+\bullet}$2×CH$_2$CHCH$_3$); HRMS calcd for C$_{35}$H$_{37}$NO$_8$ 599.2519. Found 599.2519.

EXAMPLE 8

10-Deoxylamellarin K (Compound 35)

10-Deoxylamellarin K. Aluminium chloride (80.3 mg, 0.60 mmol) was added to a solution of 10-deoxylamellarin K diisopropylether (120 mg, 0.20 mmol) in dry $CH_2Cl_2$ (10.0 mL) and the reaction allowed to stir for 1 h. After this time the reaction mixture was treated with $NH_4Cl$ (a saturated solution in $H_2O$, 10 mL). The two phases were transfered to a separatory funnel, diluted with ethyl acetate (40 mL) and washed with $H_2O$ (40 mL). The aqueous layer was extracted with ethyl acetate (2×20 mL). The combined organic phases were dried ($MgSO_4$) and concentrated on to silica gel (2 g). The residue was subjected to flash chromatography on silica gel (sequential elution with 20:1, 10:1 $CH_2Cl_2$/methanol) the relevant fractions ($R_f$ 0.7 10:1 $CH_2Cl_2$/methanol) were concentrated giving 10-deoxylamellarin K (91.7 mg, 89%) as white solid mp, 2924° C. IR (KBr disc, $cm^{-1}$) 3529, 3105, 3003, 2937, 2833, 1667, 1609, 1546, 1520, 1486, 1464, 1439, 1416, 1274, 1217, 1163, 1047. $^1H$ NMR (300 MHz, $CDCl_3$) δ7.13 (d, J=8.1 Hz, 1H), 7.08 (dd, J=1.5, 8.1 Hz, 1H), 6.98 (d, J=1.5 Hz, 1H), 6.96 (s, 1H), 6.76 (s, 1H), 6.71 (s, 1H), 6.64 (s, 1H), 5.76 (s, 1H), 5.74 (s, 1H), 4.96 (m, 1H), 4.64 (m, 1H), 3.90 (s, 3H), 3.87 (s, 3H), 3.51 (s, 3H), 3.38 (s, 3H), 3.11 (m, 2H), $^1H$ NMR (300 MHz, $d_6$DMSO) δ9.40 (s, 1H), 9.09 (s, 1H), 6.99 (d, J=8.1 Hz, 1H), 6.96 (d, J=1.5 Hz, 1H), 6.85 (dd, J=1.5, 8.1 Hz, 1H), 6.82 (s, 1H), 6.74 (s, 1H), 6.67 (s, 1H), 6.59 (s, 1H), 4.62 (m, 2H), 3.78 (s, 6H), 3.39 (s, 3H), 3.27 (s, 3H), 3.05 (br t, J=7.0 Hz, 2H). $^{13}C$ NMR+APT (75.5 MHz, $d_6$DMSO) δ152.8 (C), 147.0 (C), 146.7 (C), 145.3 (C), 145.0 (C), 144.9 (C), 144.1 (C), 142.7 (C), 133.8 (C), 126.2 (C), 124.8 (C), 123.9 (C), 121.8 (CH), 117.9 (C), 114.5 (CH), 113.0 (C), 112.8 (CH), 111.0 (C), 109.7 (C), 107.3 (C), 107.0 (CH), 103.4 (CH), 101.9 (CH), 54.3 ($CH_3$), 53.8 ($CH_3$), 53.4 ($CH_3$), 52.9 ($CH_3$), 40.3 ($CH_2$), 26.3 ($CH_2$). MS (70 eV) m/z (%): 515 (100, $M^{+\cdot}$), 257.5 (19, $M^{2+}$); HRMS calcd for $C_{29}H_{25}NO_8$ 515.1580. Found 515.1576.

EXAMPLE 9

Lamellarin U diisopropylether (Compound 38)

Lamellarin U diisopropylether. 3,4-Dihydro-6,7-dimethoxyisoquinoline (425 mg, 2.23 mmol) was added to a solution of 1-(α-iodoacetoxy)-2-[(3-isopropoxy4-methoxy-phenyl)ethynyl]-5-isopropoxy-4-methoxybenzene (1.00 g, 1.86 mmol) in dry 1,2-dichloroethane (30.0 mL) and the solution stirred at 18° C. for 17 h. After this time diisopropylethylamine (340 μL, 1.95 mmol) was added and the reaction mixture heated at 83° C. for 20 h. The reaction mixture was cooled, evaporated on to silica gel (5 g) and the residue subjected to flash chromatography on silica gel (elution with 9:1 $CH_2Cl_2$/ether) concentration of the appropriate fractions ($R_f$ 0.5 7:1 $CH_2Cl_2$/ether) gave the title compound (780 mg, 70%) as a white solid, mp 213–4° C. IR (KBr disc, $cm^{-1}$) 2975, 2936, 2836, 1694, 1620, 1608, 1580, 1542, 1511, 1485, 1463, 1440, 1415, 1271, 1259, 1241, 1213, 1167, 1043. $^1H$ NMR (300 MHz, $CDCl_3$) δ7.01 (br s, 2H), 7.03 (s, 1H), 6.87 (s, 1H), 6.74 (s, 1H), 6.69 (s, 1H), 6.65 (s, 1H), 4.75 (m, 2H), 4.50 (m, 2H), 3.90 (s, 3H), 3.86 (s, 3H), 3.41 (s, 311), 3.35 (s, 3H), 3.10 (br t, J=6.9 Hz, 2H), 1.34 (d, J=6.0 Hz, 6H), 1.32 (d, J=6.0 Hz, 6H). $^{13}C$ NMR+APT (75.5 MHz, $CDCl_3$) δ155.6 (C), 149.9 (C), 148.8 (C), 147.9 (C), 147.4 (C), 146.9 (C), 146.4 (C), 145.9 (C), 135.8 (C), 128.2 (C), 127.8 (C), 126.5 (C), 123.6 (CH), 120.0 (C), 117.7 (CH), 114.8 (C), 113.6 (C), 112.5 (CH), 110.9 (CH), 110.3 (C), 108.5 (CH), 104.8 (CH), 103.3 (CH), 71.3 (CH), 71.2 (CH), 56.3 ($CH_3$), 55.9 ($CH_3$), 55.5 ($CH_3$), 55.1 ($CH_3$), 42.3 ($CH_2$), 28.6 ($CH_2$), 21.9 ($CH_3$), 21.8 ($CH_3$). MS (70 eV) m/z (%): 599 (100, $M^{+\cdot}$), 557 (81, $M^{+\cdot}-CH_2CHCH_3$), 515 (41, $M^{+\cdot}2\times CH_2CHCH_3$); HRMS calcd for $CH_{35}H_{37}NO_8$ 599.2519. Found 599.2526.

EXAMPLE 10

Lamellarin U (Compound 29)

Lamellarin U: Aluminium chloride (315.8 mg, 2.36 mmol) was added to a solution of lamellarin U diisopropy-lether (430.0 mg, 0.717 mmol) in dry $CH_2Cl_2$ (20.0 mL) and the reaction allowed to stir for 14 h. After this time the reaction mixture was treated with $NH_4Cl$ (a saturated solution in $H_2O$, 10 mL). The two phases were transferred to a separatory funnel, diluted with ethyl acetate (40 mL) and washed with $H_2O$ (20 mL). The aqueous layer was extracted with ethyl acetate (2×20 mL). The combined organic phases were dried ($MgSO_4$) and concentrated on to silica gel (2 g). The residue was subjected to flash chromatography on silica gel (sequential elution with 20:1, 10:1 $CH_2Cl_2$/methanol) the relevant fractions ($R_f$ 0.7 10:1 $CH_2Cl_2$/methanol) were concentrated giving lamellarin U (347.1 mg, 94%) as white solid, mp 242–3 ûC. IR (KBr disc, $cm^{-1}$) 3526, 3449, 3296, 3001, 2954, 2838, 1683, 1674, 1609, 1584, 1485, 1464, 1440, 1413, 1273, 1247, 1215, 1171, 1048. $^1H$ NMR (300 MHz, $d_6$DMSO) δ9.67 (s, 1H), 9.30 (s, 1H), 7.15 (d, J=8.1 Hz, 1H), 6.98 (s, 1H), 6.90 (m, 2H), 6.80 (s, 1H), 6.69 (s, 2H), 4.62 (m, 2H), 3.84 (s, 3H), 3.78 (s, 3H), 3.39 (s, 3H), 3.26 (s, 3H), 3.11 (br t, J=7.0 Hz, 2H). $^{13}C$ NMR+APT (75.5 MHz, $d_6$DMSO) δ154.6 (C), 149.2 (C), 148.0 (C), 147.9 (C), 147.3 (C), 146.0 (C), 144.8 (C), 135.7 (C), 127.7 (C), 127.6 (C), 127.3 (C), 122.0 (CH), 119.6 (C), 118.2 (CH), 114.7 (C), 113.8 (CH), 112.9 (C), 112.1 (CH), 109.0 (C), 108.9 (CH), 105.4 (CH), 103.4 (CH), 56.4 ($CH_3$), 55.9 ($CH_3$), 55.4 ($CH_3$), 54.8 ($CH_3$), 42.9 ($CH_2$), 28.0 ($CH_2$). MS (70 eV) m/z (%): 515 (100, $M^{+\cdot}$), 257.5 (15, $M^{2+}$); HRMS calcd for $C_{28}H_{25}NO_8$ 515.1580. Found 515.1586.

EXAMPLE 11

Lamellarin W diisopropylether (Compound 11)

Lamellarin W diisopropylether: DDQ (219 mg 0.963 mmol) was added to a solution of lamellarin T diisopropyl ether (485 mg, 0.77 mmol) in dry chloroform (10 mL) and the reaction stirred at 61° C. for 2 h. The reaction mixture was cooled, evaporated on to silica gel (3 g) and the residue subjected to flash chromatography on silica gel (sequential elution with(9:1, 4:1 $CH_2Cl_2$/ether) concentration of the appropriate fractions ($R_f$ 0.6 6:1 $CH_2Cl_2$/ether) gave the title compound (479 mg, 99%) as a white solid, mp 200–1° C. IR (KBr disc, $cm^{-1}$) 2975, 2935, 2834, 1698, 1621, 1606, 1536, 1498, 1480, 1453, 1429, 1418, 1395, 1260, 1233, 1177, 1137, 1117, 1073, 1045, 975. $^1H$ NMR(300 MHz, $CDCl_3$) δ9.21 (d, J=7.8 Hz, 1H), 7.38 (d, J=7.8 Hz, 1H), 7.17 (brs, 2H), 7.14 (s, 1H), 7.01 (s, 1H), 6.97 (s, 1H), 6.72 (s, 1H), 4.58 (m, 2H), 4.03 (s, 3H), 3.97 (s, 3H), 3.94 (s, 3H), 3.46 (s, 6H), 1.41 (d, J=6.3 Hz, 6H), 1.36 (d, J=6.0 Hz, 6H). $^{13}C$ NMR+APT (75.5 MHz, $CDCl_3$) δ155.5 (C), 153.2 (C), 150.2 (C), 148.4 (C), 1487.2 (C), 147.9 (C), 146.6 (C), 146.5 (C), 142.6 (C), 133.8 (C), 129.3 (C), 128.1 (C), 124.0 (CH), 122.8 (CH), 121.3 (C), 119.3 (C), 114.1 (CH), 112.7 (CH), 111.9 (C), 109.8 (C), 108.1 (C), 106.8 (CH), 105.4 (CH), 103.3 (CH), 101.5 (CH), 71.3 (CH), 71.2 (CR), 61.6 ($CH_3$), 61.1 ($CH_3$), 56.4 ($CH_3$), 55.4 ($CH_3$), 55.1 ($CH_3$), 21.9 ($CH_3$), 21.8 ($CH_3$). MS (70 eV) m/z (%): 627 (100, $M^{+\cdot}$), 585 (85, $M^{+\cdot}-CH_2CHCH_3$); HRMS calcd for $CH_{36}H_{37}NO_9$ 627.2468. Found 627.2475.

EXAMPLE 12

Lamellarin W (Compound 9)

Lamellarin W: Aluminium chloride (112 mg, 0.836 mmol) was added to a solution of lamellarin W diisopropylether (175 mg, 0.279 mmol) in dry $CH_2Cl_2$ (10.0 mL) and the reaction allowed to stir for 14 h. After this time the reaction mixture was treated with $NH_4Cl$ (a saturated solution in $H_2O$, 5 mL). The two phases were transferred to a separatory funnel, diluted with $H_2O$ (40 mL) and extracted with ethyl acetate (3×40 mL) and washed. The combined organic phases were dried ($MgSO_4$) and concentrated on to silica gel (2 g). The residue was subjected to flash chromatography on silica gel (sequential elution with 99:1, 20:1 $CH_2Cl_2$/methanol) the relevant fractions ($R_f$ 0.2 20:1 $CH_2Cl_2$/methanol) were concentrated giving lamellarin W (143 mg, 94%) as white solid, mp 284–6° C. IR (KBr disc, $cm^{-1}$) 3413, 3135, 2937, 2841, 1667, 1606, 1481, 1424, 1275, 1240, 1207, 1156, 1075, 1045. $^1$H NMR (300 MHz, $d_6$DMSO) δ9.50 (br s, 2H), 8.89 (d, J=7.8 Hz, 1H), 7.28 (d, J=7.8 Hz, 1H), 7.09 (d, J=8.1 Hz, 1H), 6.96 (s, 2H), 6.87 (d, J=8.1 Hz, 1H),6.82 (s, 1H), 6.67 (s, 1H), 3.92 (s, 3H), 3.84 (s, 3H), 3.81 (s, 3H), 3.37 (s, 6H). $^{13}$C NMR+APT (75.5 MHz, $d_6$DMSO) δ154.8 (C), 152.4 (C), 147.5 (C), 147.1 (C), 146.9 (C), 146.8 (C), 146.0 (C), 143.9 (C), 141.4 (C), 133.0 (C), 128.8(C), 127.4 (C), 121.9 (CH), 121.8 (CH), 120.6 (C), 118.4 (C), 117.7 (CH), 111.7 (CH), 111.3 (C), 108.3 (C), 107.7 (C), 106.0 (CH), 104.8 (C), 103.3 (CH), 101.2 (CH), 61.0 ($CH_3$), 60.3 ($CH_3$), 55.6 ($CH_3$), 54.7 ($CH_3$), 54.4 ($CH_3$). MS (70 eV) m/z (%): 543 (100, $M^{+}$), 271.5 (11, $M^{2+}$); HRMS calcd for $_{30}H_{19}NO_9$ 543.1529. Found 543.1533.

TABLE 1

| Compound | $R^1$ | $R^2$ | $R^3$ | $R^4$ | $R^5$ | $R^6$ |
|---|---|---|---|---|---|---|
| 1 | H | H | H | H | H | H |
| 2 (Lamellarin B) | OMe | OMe | OMe | H | H | OMe |
| 3 (Lamellarin D) | H | OH | OMe | H | H | OMe |
| 4 (Lamellarin D-triacetate) | H | OAc | OMe | H | H | OMe |
| 5 (Lamellarin M) | OH | OMe | OMe | H | H | OMe |
| 6 (Lamellarin M-triacetate) | OAc | OMe | OMe | H | H | OMe |
| 7 (Lamellarin N) | H | OH | OMe | H | H | OMe |
| 8 (Lamellarin N-triacetate) | H | OAc | OMe | H | H | OMe |
| 9 (Lamellarin W) | OMe | OMe | OMe | H | H | OMe |
| 10 (Lamellarin k) | OH | OMe | OMe | H | H | OMe |
| 11 | OMe | OMe | OMe | H | H | OMe |

| Compound | $R^7$ | $R^8$ | $R^9$ | $R^{10}$ | $R^{11}$ | $R^{12}$ | $R^{13}$ |
|---|---|---|---|---|---|---|---|
| 1 | H | H | H | H | H | H | H |
| 2 (Lamellarin B) | OH | H | H | OMe | OH | H | H |
| 3 (Lamellarin D) | OH | H | H | OMe | OH | H | H |
| 4 (Lamellarin D-triacetate) | OAc | H | H | OMe | OAc | H | H |
| 5 (Lamellarin M) | OH | H | H | OMe | OH | H | H |
| 6 (Lamellarin M-triacetate) | OAc | H | H | OMe | OAc | H | H |
| 7 (Lamellarin N) | OH | H | H | OH | OMe | H | H |
| 8 (Lamellarin N-triacetate) | OAc | H | H | OAc | OMe | H | H |
| 9 (Lamellarin W) | OH | H | H | OH | OMe | H | H |
| 10 (Lamellarin X) | OH | H | H | OH | OMe | H | H |
| 11 | O$^i$Pr | H | H | O$^i$Pr | OMe | H | H |

TABLE 2

| Compound | $R^1$ | $R^2$ | $R^3$ | $R^4$ | $R^5$ | $R^6$ |
|---|---|---|---|---|---|---|
| 12 (Lamellarin A) | OMe | OMe | OMe | H | H | OMe |
| 13 (Lamellarin C) | OMe | OMe | OMe | H | H | OMe |
| 14 (Lamellarin E) | OH | OMe | OMe | H | H | OMe |
| 15 (Lamellarin F) | OH | OMe | OMe | H | H | OMe |
| 16 (Lamellarin G) | H | OH | OMe | H | H | OH |
| 17 (Lamellarin H) | H | OH | OH | H | H | OH |

TABLE 2-continued

[Structure diagram showing a polycyclic compound with substituents R¹–R¹⁴]

| Compound | R² | R³ | R⁴ | R⁵ | R⁶ |
|---|---|---|---|---|---|
| 18 (Lameliarin I) | OMe | OMe | OMe | H | H | OMe |
| 19 (Lamellarin I-acetate) | OMe | OMe | OMe | H | H | OMe |
| 20 (Lamellarin J) | H | OH | OMe | H | H | OMe |
| 21 (Lamellarin K) | OH | OMe | OMe | H | H | OMe |
| 22 (Lamellarin K-triacetate) | OAc | OMe | OMe | H | H | OMe |
| 23 (Lamellarin L) | H | OH | OMe | H | H | OMe |
| 24 (Lamellarin L-triacetate) | H | OAc | OMe | H | H | OMe |
| 25 (Lamellarin S) | H | OH | OMe | H | H | OH |
| 26 (Lamellarin T) | OMe | OMe | OMe | H | H | OMe |
| 27 (Lamellarin T20-sulfate) | OMe | OMe | OMe | H | H | OMe |
| 29 (Lamellarin U) | H | OMe | OMe | H | H | OMe |
| 30 (Lamellarin U20-sulfate) | H | OMe | OMe | H | H | OMe |
| 31 (Lamellarin V) | OMe | OMe | OMe | H | H | OMe |
| 32 (Lamellarin V20-sulfate) | OMe | OMe | OMe | H | H | OMe |
| 33 (Lamellarin Y20-sulfate) | H | OMe | OH | H | H | OMe |
| 34 | H | OMe | OMe | H | H | OMe |
| 35 | H | OMe | OMe | H | H | OMe |
| 36 | O$^i$Pr | OMe | OMe | H | H | OMe |
| 37 | OMe | OMe | OMe | H | H | OMe |
| 38 | H | OMe | OMe | H | H | OMe |
| 39 (Lamellarin T diacetate) | OMe | OMe | OMe | H | H | OMe |

| Compound | R⁷ | R⁸ | R⁹ | R¹⁰ | R¹¹ | R¹² | R¹³ | R¹⁴ |
|---|---|---|---|---|---|---|---|---|
| 29 (Lamellarin U) | OH | H | H | OH | OMe | H | H | H |
| 30 (Lamellarin U20-sulfate) | OSO3Na | H | H | OH | OMe | H | H | H |
| 31 (Lamellarin V) | OH | H | H | OH | OMe | H | H | OH |
| 32 (Lamellarin V20-sulfate) | OSO3Na | H | H | OH | OMe | H | H | OH |
| 33 (Lamellarin Y20-sulfate) | OSO3Na | H | H | OH | OMe | H | H | H |
| 34 | O$^i$Pr | H | H | OMe | O$^i$Pr | H | H | H |
| 35 | OH | H | H | OMe | OH | H | H | H |
| 36 | O$^i$Pr | H | H | OMe | O$^i$Pr | H | H | H |
| 37 | O$^i$Pr | H | H | O$^i$Pr | OMe | H | H | H |
| 38 | O$^i$Pr | H | H | O$^i$Pr | OMe | H | H | H |
| 39 (Lamellarin T diacetate) | OAc | H | H | OAc | OMe | H | H | H |

What is claimed is:

1. A method for the preparation of a compound of general Formula (I):

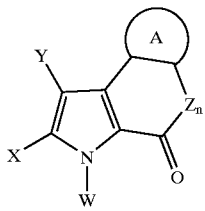

or pharmaceutically acceptable derivatives and salts, racemates, isomers and/or tautomers thereof comprising the step of cyclizing an azomethine ylide of general Formula (II):

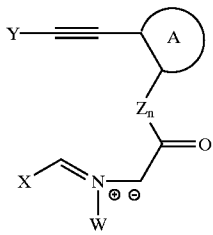

wherein,

A is a cyclic group being an optionally substituted aryl group;

Z is oxygen;

n is 1; and

Y is selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, and W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group.

2. A method according to claim 1, wherein A is selected from benzene, naphthalene, pyridine, furan, pyrrole, thiophene, quinoline, indole, benzofuran or benzothiophene, each of which may be optionally substituted.

3. A method according to claim 2, wherein A is optionally substituted benzene.

4. A method according to claim 1, wherein W and X, together with the respective nitrogen and carbon atoms to which they are attached, form an optionally substituted saturated or unsaturated nitrogen containing heterocyclic group, which may optionally be fused to a saturated or unsaturated carbocyclic group, aryl group or heterocyclic group.

5. A method according to claim 4, wherein W and X, together with the respective nitrogen and carbon atoms to which they are attached, form a group of Formula (i):

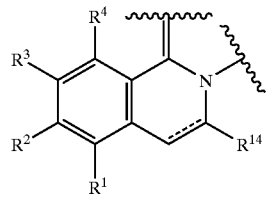

wherein ═ is an optional double bond and $R^1$–$R^4$ and $R^{14}$ may be the same or different and each are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, or any two adjacent $R^1$–$R^4$, together with the carbon atoms to which they are attached, form a saturated or unsaturated nitrogen containing heterocyclic group which may be optionally substituted or optionally fused to a saturated or unsaturated carbocyclic group, aryl group or heterocyclic group.

6. A method according to claim 5, wherein $R^1$–$R^4$ and $R^{14}$ are selected from hydrogen, hydroxy, optionally substituted alkyl, acyl or sulfate.

7. A method according to claim 1, wherein Y is an optionally substituted phenyl group of Formula (ii):

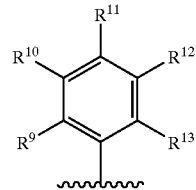

wherein $R^9$–$R^{13}$ may be the same or different and each are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, or any two adjacent $R^9$–R13, together with the carbon atoms to which they are attached, form a saturated or unsaturated nitrogen containing heterocyclic group which may be optionally substituted or optionally fused to a saturated or unsaturated carbocyclic group, aryl group or heterocyclic group.

8. A method according to claim 7, wherein $R^9$–$R^{13}$ are selected from hydrogen, hydroxy, optionally substituted alkyl, optionally substituted alkoxy, and acyloxy.

9. A method according to claim 8, wherein the $R^9$–$R^{13}$ are selected from hydrogen, hydroxy, methoxy, isopropoxy, methyl and acetoxy.

10. A method for the preparation of a compound of Formula (Ia):

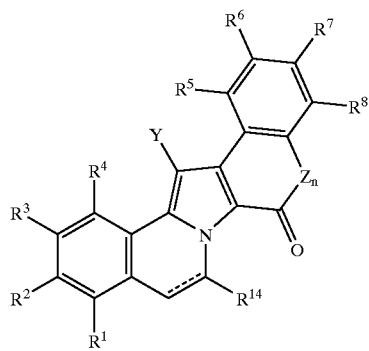

comprising the step of cyclizing an azomethine ylide of general Formula (IIa):

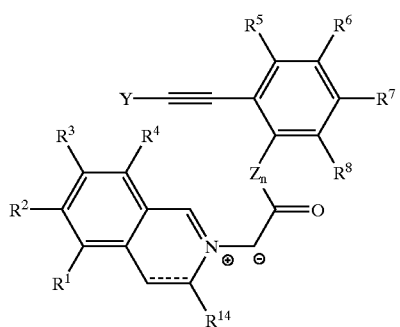

wherein $R^1$–$R^8$, $R^{14}$ and Y may be the same or different and each are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

Z is oxygen; and n is 1.

11. A method for the preparation of a compound of Formula (Ib)

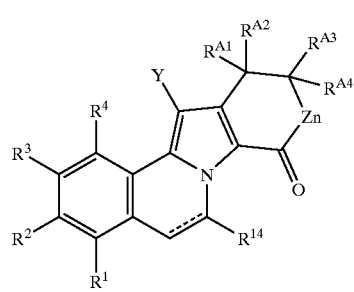

comprising the step of cyclizing an azomethine ylide of general Formula (IIb).

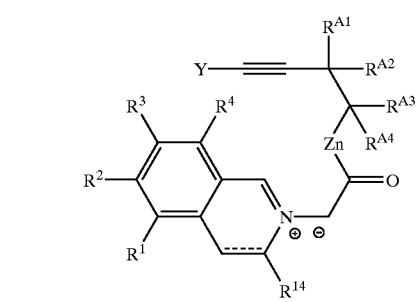

wherein $R^1$–$R^{14}$, $R^{14}$ and Y may be the same or different and each are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

Z is oxygen;

n is 1 and $R^{A1}R^{A2}C$—$CR^{A3}R^{A4}$ form a cyclic group which is an optionally substituted aryl group.

12. A method according to claim 11 wherein $R^{A1}$–$R^{A4}$ are hydrogen.

13. A method according to claim 10 or claim 11, wherein Y is an optionally substituted phenyl group of Formula (ii):

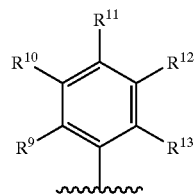

wherein $R^9$–$R^{13}$ may be the same or different and each are selected from hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano.

14. A method according to claim 13 wherein $R^9$–$R^{13}$ are selected from hydrogen, hydroxy, optionally substituted alkoxy, optionally substituted alkyl, sulfate and acyloxy.

15. A method according to claim 14, wherein $R^9$–$R^{13}$ are selected from hydrogen, hydroxy, isopropoxy, methoxy, methyl, acetoxy and sulfate.

16. A method according to any one of claims 1, 10 or 11, wherein the cyclization of the azomethine ylide is achieved by thermal treatment.

17. A method according to claim 16, wherein the thermal treatment comprises heating the azomethine ylide in tetrahydrofuran, chloroform or 1,2-dichloroethane.

18. A method according to claim 17, wherein the thermal treatment further includes treatment with a metal salt.

19. A method according to claim 18, wherein the metal salt is CuI.

20. A method according to any one of claims 1, 10 or 11, wherein the cyclization is followed by oxidative treatment.

21. A method according to claim 20, wherein the oxidative treatment comprises oxidation in air.

22. A method according to claim 21, wherein the oxidative treatment in air is carried out in the presence of silica gel.

23. A method according to claim 20, wherein the oxidative treatment comprises treatment with Fremy's salt.

24. A method according to claim 20, wherein the oxidative treatment comprises treatment with a quinone.

25. A method according to claim 24, wherein the quinone is selected from chloranil or 2,3-dichloro-5,6-dicyano-1,4-benzoquinone.

26. A method according to claim 20, wherein the oxidative treatment comprises treatment with a metal catalyst.

27. A method according to claim 1, wherein the compound of Formula (II) is formed by treating a compound of Formula (III):

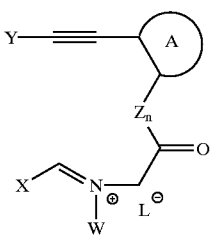

with a base, wherein

A is a cyclic group being an optionally substituted aryl group;

Z is oxygen;

n is 1; and

Y is selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, and W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group;

and the counter ion $L^{63}$ is a stable, weakly basic anion.

28. A method according to claim 10, wherein the compound of Formula (IIa) is formed by treating a compound of Formula (IIIa):

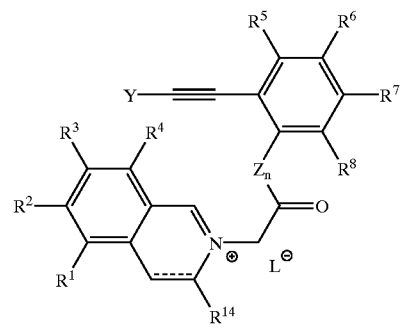

with a base, wherein $R^1$–$R^8$, $R^{14}$ and Y may be the same or different and each are selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

Z is oxygen;

n is 1; and the counter ion $L^{\ominus}$ is a stable basic anion.

29. A method according to claim 27 or claim 28, wherein $L^{\ominus}$ is a sulphonate compound or a halogen.

30. A method according to claim 29, wherein L' is selected from tosylate. mesylate, triflate, bosylate, besylate, tresylate, nonaflate, nosylate, bromide, chloride or iodide.

31. A method according to claim 27 or claim 28, wherein the base is derived from an alkali metal, or the base is a mono-, di-, or tri-substituted amine.

32. A method according to claim 31, wherein the base is an alkyl lithium or an aryl lithium.

33. A method according to claim 31, wherein the base is an alkali metal carbonate.

34. A method according to claim 31, wherein the base is an alkyl substituted amine.

35. A method according to claim 34, wherein the base is triethylamine or diisopropylethylamine.

36. A method according to claim 1, wherein the cyclization step is preceded by steps comprising:

a) coupling a compound of Formula (IV) with a compound of Formula (V):

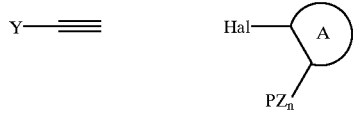

to afford the compound of Formula (VI):

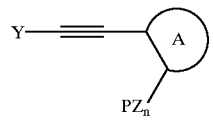

wherein $PZ_n$ is a synthon for $Z_n$;

b) unmasking $Z_n$ of compound (VI) and coupling with a compound L-CH$_2$—C(O)-L', to provide compound (VII):

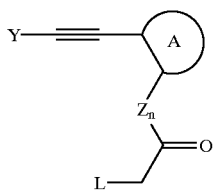

wherein L and L' are each a leaving group or a substituent convertible to a leaving group;

c) treatment of compound (VII) with an imine of Formula (VIII)

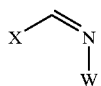

d) generation of the azomethine ylide of general formula (II);

wherein Hal is halogen;

A is a cyclic group being an optionally substituted aryl group;

Z is oxygen;

n is 1;

Y is selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, and W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group.

37. A method according to claim 10, wherein the cyclization step is preceded by steps comprising:

coupling a compound of Formula (IV) to a compound of Formula (Va):

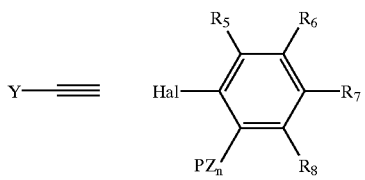

to afford the compound of Formula (VIa):

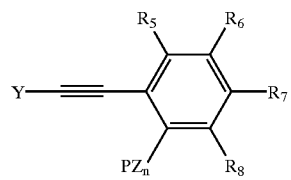

(b) unmasking $Z_n$ of compound (VIa) and coupling with a compound L-CH$_2$—C(O)-L' to provide compound (VIIa):

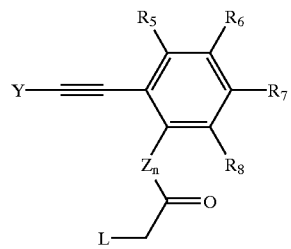

(c) treatment of compound (VIIa) with a compound of Formula (VIIIa):

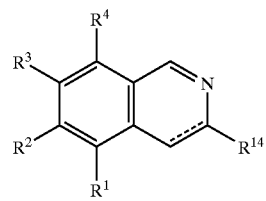

(d) generation of the azomethine ylide of general Formula (Ia);

wherein

Hal is halogen;

Z is oxygen;

n is 1;

Y is selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano;

L and L' are each a leaving group or a substituent convertible to a leaving group; and $PZ_n$ is a synthon for $Z_n$.

38. A method according to claim 36 or claim 37, wherein $PZ_n$ is OAc and unmasking refers to hydrolysis of the OAc group to provide OH.

39. A method according to claim 36 or claim 37, wherein $PZ_n$ is an aldehyde or acyl group and unmasking refers to oxidation of the aldehyde or acyl group to the corresponding ester, followed by hydrolysis.

40. A method according to claim 36 or claim 37, wherein L' is a halogen or OH converted to a leaving group.

41. A method according to claim 40, wherein L' is bromine or chlorine.

42. A method according to claim 36 or claim 37, wherein the coupling step a) is carried out in the presence a palladium catalyst.

43. A method according to claim 42, wherein the palladium catalyst is selected from PdCl$_2$(PPh$_3$)$_2$ or Pd(PPh$_3$)$_4$.

44. A method according to claim 42, wherein the coupling is mediated by a Cu(I) compound.

45. A method according to claim 36 wherein one or more of the following steps:
  (a) the coupling of a compound of Formula (IV) with a compound of Formula (V),
  (b) unmasking $Z_n$ of the compound of Formula (VI) and coupling with a compound L-CH$_2$—C(O)-L',
  (c) treatment of the compound of Formula (VII) with the imine of Formula (VIII),
is performed by combinatorial synthesis.

46. A method according to claim 42, wherein the coupling is mediated by a Cu(I) compound and wherein the palladium catalyst is selected from PdCl$_2$ (PPh$_3$)$_2$ or Pd(PPh$_3$)$_4$.

47. A method for the preparation of a fused polycyclic compound comprising the step of:
  cyclizing an azomethine ylide of general Formula (II):

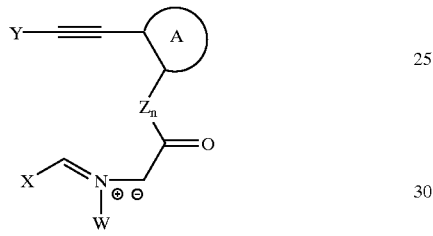

wherein,
A is a cyclic group being an optionally substituted aryl group;
Z is oxygen;
n is 1; and
Y is selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, and W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group.

48. A method for the preparation of a compound of general Formula (I):

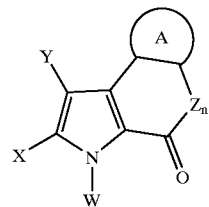

or pharmaceutically acceptable derivatives and salts, racemates, isomers and/or tautomers thereof comprising the step of cyclizing an azomethine ylide of general Formula (II):

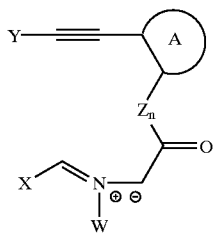

wherein,
A is a cyclic group being an optionally substituted aryl group;
Z is oxygen;
n is 1; and
Y is selected from the group consisting of: hydrogen, optionally substituted alkyl, optionally substituted alkenyl, optionally substituted alkynyl, optionally protected hydroxy, optionally substituted amino, optionally substituted alkoxy, optionally substituted alkenoxy, optionally substituted alkynoxy, optionally substituted aryl, optionally substituted heterocyclyl, carboxy, carboxy ester, carboxamido, acyl, acyloxy, mercapto, optionally substituted alkylthio, halogen, nitro, sulfate, phosphate and cyano, and W and X, together with the nitrogen and carbon atoms to which they are attached, form a saturated or unsaturated nitrogen containing heterocyclic group which may be optionally substituted or optionally fused to a saturated or unsaturated carbocyclic group, aryl group or heterocyclic group.

* * * * *

UNITED STATES PATENT AND TRADEMARK OFFICE
CERTIFICATE OF CORRECTION

PATENT NO. : 6,521,757 B1
DATED : February 18, 2003
INVENTOR(S) : Banwell et al.

It is certified that error appears in the above-identified patent and that said Letters Patent is hereby corrected as shown below:

Title page,
Item [57], ABSTRACT,
Line 9, replace "of" with -- or --.
Line 11, replace "alkinoxy" with -- alkenoxy --.

Column 6,
Line 18, replace "$R^3$" with -- $R^{A3}$ --.
Line 22, replace "dihydrophyran" with -- dihydropyran --.
Line 41, insert -- are -- between "$R^9$-$R^{13}$" and "hydrogen".

Column 12,
Scheme $1^a$, replace the second incidence of "(b)(i)", along the downward pointing arrow, with -- (b)(ii) --.

Column 18,
Replace "10-deoxlamellarim K" with -- 10-deoxylamellarin K --.

Column 23,
Line 3, replace "methacrylie" with -- methacrylic --.
Line 49, replace "dycano" with -- dicyano --.

Column 25,
Line 10, replace "300 MH" with -- 300 MHz --.
Line 49, replace "2-lodo5" with -- 2-lodo-5 --.
Line 57, replace "Na2S$_2$O$_5$" with -- $Na_2S_2O_5$ --.

Column 26,
Line 1, replace "MH" with -- MHz --.
Line 2, replace "47.9" with -- 147.9 --.
Line 9, replace "(0.1 g" with -- (10.1g --.
Line 10, replace "PP$_3$" with -- $PPh_3$ --.
Line 26, replace "1510.1464" with -- 1510, 1464 --.
Line 35, replace "—CH)" with -- -$CH_3$ --.
Line 43, replace "TBF" with -- THF --.
Line 65, replace "(s, 31)" with -- (s, 3H) --.
Line 66, replace "MH" with -- MHz --.

Column 27,
Line 7, replace "1H" with -- H --.
Line 20, replace "NH3" with -- $NH_3$ --.

UNITED STATES PATENT AND TRADEMARK OFFICE
CERTIFICATE OF CORRECTION

PATENT NO. : 6,521,757 B1
DATED : February 18, 2003
INVENTOR(S) : Banwell et al.

It is certified that error appears in the above-identified patent and that said Letters Patent is hereby corrected as shown below:

Column 28,
Line 5, replace "$C_24H_27O_6I$" with -- $C_{24}H_{27}O_6I$ --.
Line 35, replace "$(CH_3), (CH_3).$" with -- $(CH_3), 21.8 (CH_3), 21.7 (CH_3).$ --.

Column 29,
Line 16, replace "$PP_3$" with -- $PPh_3$ --.

Column 33,
Line 52, replace "(s, 311)" with -- (s, 3H) --.

Column 34,
Line 40, replace "5 1498" with -- 1498 --.

Column 35,
Line 11, replace "$\overline{\phantom{C}}C$" with -- $^{13}C$ --.

Column 37,
Table 2, after "Compound $R^7$ $R^8$ $R^9$ $R^{10}$ $R^{11}$ $R^{12}$ $R^{13}$ $R^{14}$", insert

| | | | | | | | |
|---|---|---|---|---|---|---|---|
| 12 Lamellarin A | OH | H | H | OMe | OH | H | H | OH |
| 13 Lamellarin C | OH | H | H | OMe | OH | H | H | H |
| 14 Lamellarin E | OH | H | H | OH | OMe | H | H | H |
| 15 Lamellarin F | OH | H | H | OMe | OMe | H | H | H |
| 16 Lamellarin G | OMe | H | H | OH | OMe | H | H | H |
| 17 Lamellarin H | OH | H | H | OH | OH | H | H | H |
| 18 Lamellarin I | OH | H | H | OMe | OMe | H | H | H |
| 19 Lamellarin I-acetate | OAc | H | H | OMe | OMe | H | H | H |
| 20 Lamellarin J | OH | H | H | OMe | OMe | H | H | H |
| 21 Lamellarin K | OH | H | H | OMe | OH | H | H | H |
| 22 Lamellarin K-triacetate | OAc | H | H | OMe | OAc | H | H | H |
| 23 Lamellarin L | OH | H | H | OH | OMe | H | H | H |
| 24 Lamellarin L-triacetate | OAc | H | H | OAc | OMe | H | H | H |
| 25 Lamellarin S | OH | H | H | OH | OH | H | H | H |
| 26 Lamellarin T | OH | H | H | OH | OMe | H | H | H |
| 27 (Lamellarin T20-sulfate) | OS03Na | H | H | OMe | OH | H | H | H |

UNITED STATES PATENT AND TRADEMARK OFFICE
CERTIFICATE OF CORRECTION

PATENT NO.    : 6,521,757 B1
DATED         : February 18, 2003
INVENTOR(S)   : Banwell et al.

It is certified that error appears in the above-identified patent and that said Letters Patent is hereby corrected as shown below:

Column 40,
Line 54, replace "$R^9$-R13" with -- $R^9$-$R^{13}$ --.

Column 41,
Line 67, replace "(IIb)." with -- (IIb): --.

Column 42,
Line 15, replace "$R^1$-$R^{14}$" with -- $R^1$-$R^4$ --.

Column 43,
Line 63, replace "$L^{63}$" with -- $L^{\ominus}$ --.

Column 44,
Line 34, replace "L'" with -- $L^{\ominus}$ --.

Column 46,
Line 39, replace "(Ia)" with -- (IIa) --.

Column 47,
Line 2, insert -- of -- between "presence" and "a".

Signed and Sealed this

Twenty-seventh Day of July, 2004

JON W. DUDAS
*Acting Director of the United States Patent and Trademark Office*